United States Patent [19]
Cook et al.

[11] Patent Number: 5,981,187
[45] Date of Patent: Nov. 9, 1999

[54] SELECTION METHOD INVOLVING ACETAL COENZYME A SYNTHETASE IN CALVES

[75] Inventors: Robert M. Cook, Laingsburg; Ahmed M. Raafat, Okemos, both of Mich.

[73] Assignee: Board of Trustees operating Michigan State University, East Lansing, Mich.

[21] Appl. No.: 08/918,966

[22] Filed: Aug. 26, 1997

Related U.S. Application Data

[62] Division of application No. 08/613,965, Mar. 8, 1996.
[51] Int. Cl.$^6$ ............................. C12G 1/68; C12G 1/00; G01N 33/53; C12P 21/06
[52] U.S. Cl. ............................. 435/6; 435/7.1; 435/69.1; 435/4
[58] Field of Search ..................... 435/7.1, 6, 4; 530/550

[56] References Cited

U.S. PATENT DOCUMENTS 5,041,371  8/1991  Cowan et al. .

OTHER PUBLICATIONS

Mellenberger, B.W., et al., Biochem. J. 136:741 (1973).
Marinez, D. I., et al., J. Agric. Food Chem. 24:927 (1976).
Ricks, C.A. and R.M. Cook, J. Dairy Sci. 64:2324 (1981).
Reynolds, C.K. et al., J. Dairy Sci. 71:2395 (1988).
Amaral, D.M. et al., J. Dairy Sci. 73:1244 (1990).
Glisin, et al., Biochemistry 13:2633 (1974(.
Ullrich et al, Science. 196–1313 (1977).
Lehrach et al., Biochemistry 16:4743 (1977).
Goldberg., Proc. Natl. Acad. Sci. 77:5794 (1980).
Okayama and Berg., Mol. Cell. Biol. 2:161 (1982).
Gubler and Hoffman, Gene/ 25:263 (1983).
McDonell et al., J. Mol. Biol. 110:119 (1977).
Weiss, et al., J. Biol. Chem. 243:4543 (1968).
Young, R.A. and R.W. Davis. Proc. Natl. Acad. Sci. 80:1194 (1983).
Young, R.A. and R.W.Davis, Science 222:778 (1983).
Qureshi, S. and R.M. Cook, J. Agric. Food Chem. 23:555 (1975).
Mierendorf, R.C., et al., Methods Enzumol. 152:458 (1987).
Grunert, R.R. and P.H. Phillips, Arch. Biochem. 30:217 (1951).
Yamamoto, K.R., et al., Virology 40:734 (1970).
Vande Woude, G.F. et al., Proc. Natl. Acad. Sci. 76:4464 (1979).
Birnboim, H.C., et al., Nucleic Acids Res. 7:444 (1979).
Ish–Horowicz, D., et al., Rapid and efficient cosmid cloning. Nucleic Acids (1981).
Feinberg, A.P. and B. Vogelstein, Anal. Biochem. 132:6 (1983).
Grunstein, M. and D.S. Hogness, Proc. Natl. Acad. Sci. 72:3961 (1975).
Benton, W.C. and R.W. Davis, Science, 196:180 (1979).
Blin, N. and D.W. Stafford, Nucleic Acids Res. 3:2303 (1976).
Southern, E.M., J. Mol. Biol. 98:503 (1975).
Wreschner, D.H. and M. Herzberg, Nucleic Acids. Res. 12:1349 (1984).
Sanger, F., et al., Proc. Natl. Acad. Sci. 74:5463 (1977).
Weinberger, C. et a., Science 228:740 (1985).
Davis, B.J., Ann. N.Y. Acad. Sci. 121:404 (1964).
Towbin, H. et al., Proc. Natl. Acad. Sci. 76:4350 (1979).
Burnette, W.N. Anal. Biochem. 112:195 (1988).
Thomas, P.S., Proc. Natl. Acad. Sci. 77:5201 (1980).
White, B.A. and F.C. Bancroft, J. Biol. Chem. 257:8569 (1982).
Smith, T.F. and M.S. Waterman, Advances in Applied Mathematics. 2:482–498 (1981).
Aviv et al (1972).
Cook, R.M. et al., Agr. and Food Chem. 23:561–563 (1975).
Connerton, I.F., et al. Mol. Microbiol. 4:451–460 (1990).
Stamoudis, V., et al., J. Agric. Food Chem. 23:563 (1975).
Hiroyuki, T., Protein Seg. Data Anal. 4:111–117 (1991).
Klein–Hitpass, L., et al., Cell 60:247–257 (1990).
Struhl, K. Cell. 49:295–297 (1987).
Laybourn, J. and J. Kadonaga, Science. 254:238–244 (1991).
Blobel, G., Gene gatting: a Hypothesis. PNAS. 83:8527–8529 (1985).
Chang, D. and P. Sharp, Science, 249:614–615 (1990).
Hamel, C.P., et al., Molecular cloning and expression of RPE65, a novel retinal pigment epithelium–specific microsomal protein that is post–trans–scriptionally regulated in vitro. J.B.C. 268:15751–15757 (1993).
Shigeko, F.S., et al. Cloning and expression of murine S–Adenosylmethionine synthetase.J.B.C. 268:13978–13986 (1993).
Nishizuka, Y., Signal transduction:Crosstalk. TIBS. 17:367–376 (1992).
Marinez et al. J. Agric. Food Chem., vol. 24, No. 5, 1976.
Raafa. Ph.D. Dissertation, Michigan State Univ., 1994.
Merriam–Webster's Collegiate Dictionary. 10th Edition, 1996.
Birnboim, H.C., Methods in Enzymology, 100:243–255 (1983).
Mayes–EL: Waterfield–MD, EMBO–J. 531–537 (1984).

*Primary Examiner*—Paula K. Hutzell
*Assistant Examiner*—Lin Sun-Hoffman
*Attorney, Agent, or Firm*—Ian C. McLeod

[57] ABSTRACT

A method and test kit for deterining milk production in bovines is described. The acetyl coenzyme A synthetase (ACS) production is determined and related to milk production. The method is useful in selection and/or breeding to enhance milk production. Recombinant microganisms, plasmids and ACS is also described.

7 Claims, 18 Drawing Sheets

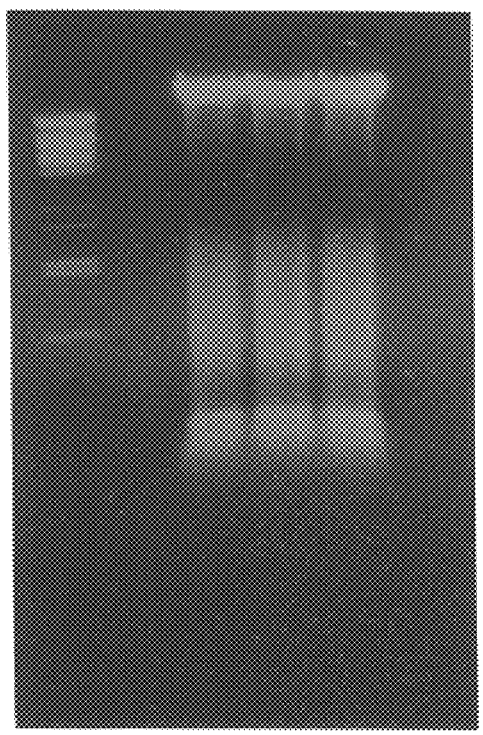
FIG. 7
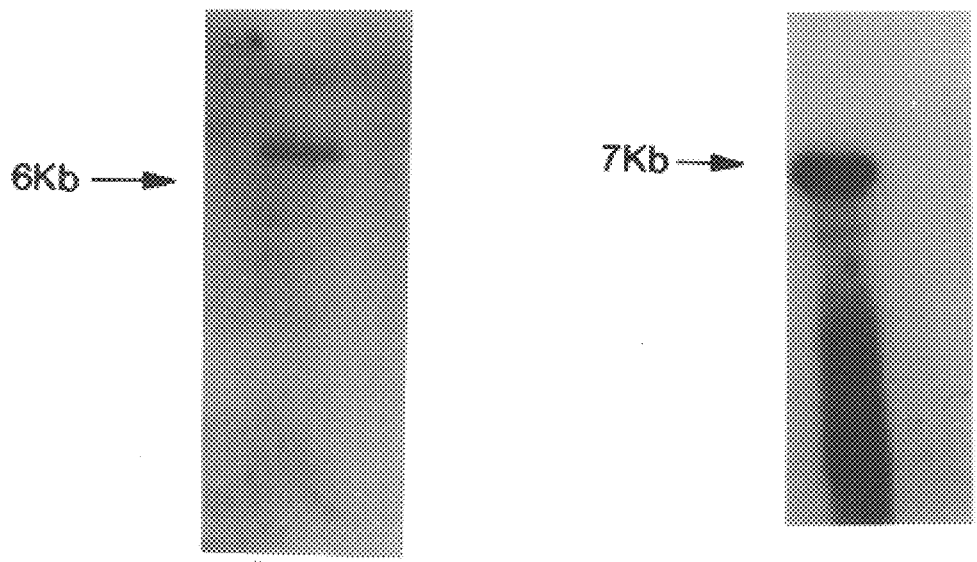
FIG. 8
FIG. 9

```
CCG TTG CTG TCG CGC ACC ACG CAC GCA GCA CAC GGC CCC GCA CAC    45
AGC CCC ATC TTA CCC ACC CTG CAA CCA ACC CCC GTC GAC TGC CTT    90
ACA CAC CCG CCC CCG CCG TCC GCC AGC ACG GGG GTG AGA ACA AGG   135
CAC TAG GTC GGC CGG CCA GCG CGA CA                            161
```

FIG. 12A

```
TGC AGG TCG ACT CTA GAG GAT CCC GGG TAC CGA GCT CGA ATT CCG    45
TTG CTG CCG TTG CTG TCG CGC GAC GCC GAC CTA GTG CCT            90
TGT TCT CAC CCC CGT GCT GGC GGA CGG ACG CCG CGC GGG GGC GGG   135
TGT GTA AGG CAG TCG ACG CGG GGG TTG GTT GCA GGG TGG GTA AGA   180
TGG GGC TGT GTG CGG GGC CGT GTG CGT GCG TGC GTG CGT GCC GGA   225
CAC                                                           228
```

FIG. 12B

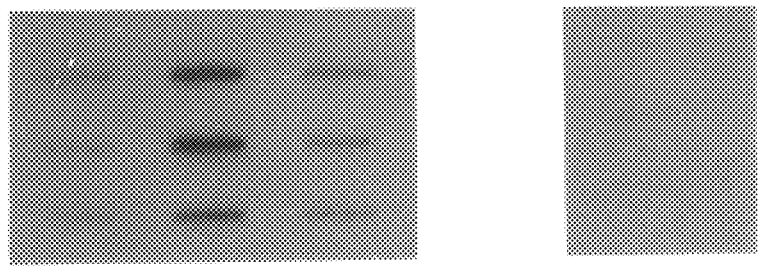
FIG. 19A
FIG. 19B
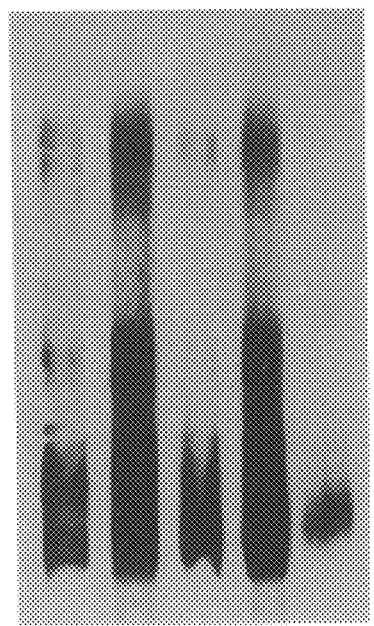
FIG. 20

```
CTC TCC CCA TCC TCC CCC CAA GAT TGC ATG CCT GCA GGT CGA CTC    45
 L   S   P   S   S   P   Q   D   C   M   P   A   G   R   L

TAG AGG ATC CCC GGG TAC CGA GCT CGA ATT CTC ATG TTT GAC AGC    90
 *   R   I   P   G   Y   R   A   R   I   L   M   F   D   S

TTA TCA CTG ATA AGC TTT AAT GCG GTA GTT TAT CAC AGT TAA ATT   135
 L   S   L   I   S   F   N   A   V   V   Y   H   S   *   I

GCT AAC GCA GGT CAG GCA CCG TGT ATG AAA TCA TAC AAT GCG CTC   180
 A   N   A   G   Q   A   P   C   M   K   S   Y   N   A   L

ATC GTC ATC CTA GGC ACC GTC ACC CTG GAT GCT GAT GGC ATG GCT   225
 I   V   I   L   G   T   V   T   L   D   A   D   G   M   A

TGG TAC GAC TGC GGC CCT TGC GGT TAT GCG TCG CGG CCT CTT GCG   270
 W   Y   D   C   G   P   C   G   Y   A   S   R   P   L   A

GAT ATC GTC CAT TCC GAC AGC ATG CCA GTC ACT ATG GCC GTG CCG   315
 D   I   V   H   S   D   S   M   P   V   T   M   A   V   P

CAG CGC TAT ATG CGT CGA TGC AAT TTC TAT GCG NAC CCG TTC ACG   360
 Q   R   Y   M   R   R   C   N   F   Y   A   X   P   F   T

GAG CAC TGT CCG ACC GCC TTT GCC GCC GCC CAG TCC TGC CGT CGC   405
 E   H   C   P   T   A   F   A   A   A   Q   S   C   R   R

TAC TTC CAG CCA CTA TCG ACT ACG CGC TCA TGG CGA CCA CAC CCG   450
 Y   F   Q   P   L   S   T   T   R   S   W   R   P   H   P

TCC TGT CGA TCC CCG GGC CCT NGC CTC TAC AGG ATC CTC TAC CCC   495
 S   C   R   S   P   G   P   X   L   Y   R   I   L   Y   P

GGA CGC ATC GTC CCC GGC ATC ACC GCC NCC ACA GGT GCG GTT GCT   540
 G   R   I   V   P   G   I   T   A   X   T   G   A   V   A

GGC GCC TAT ACG CCG ACA TCA CCG ATG GGG AAG ATC GGG CTC GCC   585
 G   A   Y   T   P   T   S   P   M   G   K   I   G   L   A

ACT TCG GGC TCA TCA GCG CTT GTT TCG GCG TGG GTA TGG TGT GCA   630
 T   S   G   S   S   A   L   V   S   A   W   V   W   C   A

GTC AGT GAT AAG TGG CGG GGG ACT GTT GGG GGC GCC ACT CCT TGC   675
 V   S   D   K   W   R   G   T   V   G   G   A   T   P   C

ATG CAC CAT TCC TTG CGG CGG CGT GCT CAA CGG CTC AAC CTA CAC   720
 M   H   H   S   L   R   R   R   A   Q   R   L   N   L   H

GGG TGC TTC GAA TGC AGG AGT GCA TGG GAG AGC TCG ACC GAT GCC   765
 G   C   F   E   C   R   S   A   W   E   S   S   T   D   A
```

FIG. 26A-I

```
TGG AGC TCA CAG AAA GCT TNC ATC CCT GCA GGC CGA CCG ATN CCC   810
 W   S   S   Q   K   A   X   I   P   A   G   R   P   X   P

TTG AGA GCC TTC AAC CCA GTC AGC TCC TTC CGG TGG GCN CGG GGC   855
 L   R   A   F   N   P   V   S   S   F   R   W   X   R   G

ATG ACT ATC GTC NNC GCA CTT ACA CTG TCT TCT TTA TCA TGC AAC   900
 M   T   I   V   X   A   L   T   L   S   S   L   S   C   N

TCG TGG GAC AGG TGC CGG CAG CGA TCT GGG TCA TTT TCG GCG AGG   945
 S   W   D   R   C   R   Q   R   S   G   S   F   S   A   R

ACC GCT TTC GCT GGA GCG CGA CGA GGA TCG GCC TGT CGC TTG CGT   990
 T   A   F   A   G   A   R   R   G   S   A   C   R   L   R

ATT CGG AAT CTT GCA CGC CCT CGT CGG AGT GTG ATG ACA CTG GTT  1035
 I   R   N   L   A   R   P   R   R   S   V   M   T   L   V

CGC TGT CCG TGC ACC TGG AAC TCC GTA TGT TCT GTC CAA GTT CCT  1080
 R   C   P   C   T   W   N   S   V   C   S   V   Q   V   P

GCT ATC GGC TTG TTC TTA AAT GCC TGT GAG AGT AGT ACA CTG TAC  1125
 A   I   G   L   F   L   N   A   C   E   S   S   T   L   Y

TGT GA                                                      1130
 C
```

FIG. 26A-2

```
TTTCTTAGAC GTCAGGTGGC ACTTTTTGGG GAAATGTGCG CGGAACCCCT ATTTGTTTAT   60

TTTTCTAAAT ACATTCAAAT ATGTATCCGC TCATGAGACA ATAACCCTGA TAAATGCTTC  120

AATAATATTG AAAAAGCAAG AGTATGAGTA TTCAACATTT CCGTGTCGCC TTATTCCTTT  180

TTTGCGGCAT TTTGCTTCCT GTTTTTTGTA CGCCTATTTT TATAGGTTAA TNTCATGATA  240

ATAATGGTTT CTTAAGACGT CA                                          262
```

FIG. 26B

SEQUENCE LISTING

```
(1) GENERAL INFORMATION:

(iii) NUMBER OF SEQUENCES:   8

(2) INFORMATION FOR SEQ ID NO:1:

(i) SEQUENCE CHARACTERISTICS:
        (A) LENGTH: 1130
        (B) TYPE:  nucleotides
        (C) STRANDEDNESS:  Single
        (D) TOPOLOGY:  Linear (ii) MOLECULE TYPE:
        (A) DESCRIPTION: cDNA (iii) HYPOTHETICAL:   No (iv) ANTI-SENSE:  No (vi) ORIGINAL SOURCE:
        (A) ORGANISM:  Bovine
        (B) STRAIN:
        (C) INDIVIDUAL ISOLATE:   ATC5
        (G) CELL TYPE:  mammary gland (ix) FEATURE:
        (A) NAME/KEY:  cDNA in pATC5
        (B) LOCATION:  mammary gland cDNA and
            encoded peptide
        (C) IDENTIFICATION METHOD:  Sequencing
```

(D) OTHER INFORMATION: Encodes a portion
of acetyl coenzyme A
synthetase (xi) SEQUENCE DESCRIPTION: SEQ ID NO:1:

```
CTC TCC CCA TCC TCC CCC CAA GAT TGC ATG CCT GCA GGT CGA CTC        45
Leu Ser Pro Ser Ser Pro Gln Asp Cys Met Pro Ala Gln Arg Leu
                5                  10                  15

TGA AGG ATC CCC GGG TAC CGA GCT CGA ATT CTC ATG TTT GAC AGC        90
    Arg Ile Pro Gly Tyr Arg Ala Arg Ile Leu Met Phe Asp Ser
                20                  25                  30

TTA TCA CTG ATA AGC TTT AAT GCG GTA GTT TAT CAC AGT TAA ATT       135
Leu Ser Leu Ile Ser Phe Asp Ala Val Val Tyr His Ser     Ile
                35                  40                  45

GCT AAC GCA GGT CAG GCA CCG TGT ATG AAA TCA TAC AAT GCG CTC       180
Ala Asp Ala Gly Gln Ala Pro Cys Met Lys Ser Tyr Asp Ala Leu
                50                  55                  60

ATC GTC ATC CTA GGC ACC GTC ACC CTG GAT GCT GAT GGC ATG GCT       225
Ile Val Ile Leu Gly Thr Val Thr Leu Asp Ala Asp Gly Met Ala
                65                  70                  75

TGG TAG GAC TGC GGC CCT TGC GGT TAT GCG TCG CGG CCT CTT GCG       270
Trp Tyr Asp Cys Gln Pro Cys Gln Tyr Ala Ser Arg Pro Leu Ala
                80                  85                  90

GAT ATC GTC CAT TCC GAC AGC ATG CCA GTC ACT ATG GCC GTG CCG       315
Asp Ile Val His Ser Asp Ser Met Pro Val Thr Met Ala Val Pro
                95                 100                 105

CAG CGC TAT ATG CGT CGA TGC AAT TTC TAT GCG NAC CCG TTC ACG       360
Gln Arg Tyr Met Arg Arg Cys Asp PHe Tyr Ala Xaa Pro Phe Thr
               110                 115                 120

GAG CAC TGT CCG ACC GCC TTT GCC GCC GCC CAG TCC TGC CGT CGC       405
Glu His Cys Pro Thr Ala Phe Ala Ala Ala Gln Ser Cys Arg Arg
               125                 130                 135

TAC TTC CAG CCA CTA TCG ACT ACG CGC TCA TGG CGA CCA CAC CCG       450
Tyr PHe Gln Pro Leu Ser Thr Thr Arg Ser Trp Arg Phe His Pro
               140                 145                 150

TCC TGT CGA TCC CCG GGC CCT NGC CTC TAC AGG ATC CTC TAC CCC       495
Ser Cys Arg Ser Pro Gly Pro Xaa Leu Tyr Arg Ile Leu Tyr Pro
               155                 160                 165

GGA CGC ATC GTC CCC GGC ATC ACC GCC NCC ACA GGT GCG GTT GCT       540
Gly Arg Ile Val Pro Gly Ile Thr Ala Xaa Thr Gly Ala Val Ala
               170                 175                 180

GGC GCC TAT ACG CCG ACA TCA CCG ATG GGG AAG ATC GGG CTC GCC       585
Gly Ala Tyr Thr Pro Thr Ser Pro Met Gly Lys Ile Gly Leu Ala
               185                 190                 195

ACT TCG GGC TCA TCA GCG CTT GTT TCG GCG TGG GTA TGG TGT GCA       630
Thr Ser Gly Ser Ser Ala Leu Val Ser Ala Trp Val Trp Cys Ala
               200                 205                 210

GTC AGT GAT AAG TGG CGG GGG ACT GTT GGG GGC GCC ACT CCT TGC       675
Val Ser Asp Lys Trp Arg Gly Thr Val Gly Cys Ala Thr Pro Cys
               215                 220                 225

ATG CAC CAT TCC TTG CGG CGG CGT GCT CAA CGG CTC AAC CTA CAC       720
Met His His Ser Leu Arg Arg Arg Ala Gln Arg Leu Asp Leu His
               230                 235                 240

GGG TGC TTC GAA TGC AGG AGT GCA TGG GAG AGC TCG ACC GAT GCC       765
Gly Cys PHe Glu Cys Arg Ser Ala Trp Glu Ser Ser Thr Asp Ala
               245                 250                 255

TGG AGC TCA CAG AAA GCT TNC ATC CCT GCA GGC CGA CCG ATN CCC       810
Trp Ser Ser Gln Lys Ala Xaa Ile Pro Ala Gly Arg Pro Xaa Pro
               260                 265                 270

TTG AGA GCC TTC AAC CCA GTC AGC TCC TTC CGG TGG GCN CGG GGC       855
Leu Arg Ala Phe Asp Pro Val Ser Ser Phe Arg Trp Xaa Arg Gly
```

-continued

```
                    275                 280                 285
ATG ACT ATC CTG NNC GCA CTT ACA CTG TCT TCT TTA TCA TGC AAC          900
Met Thr Ile Val Xaa Ala Leu Thr Leu Ser Ser Leu Ser Cys Asn
                    290                 295                 300

TCG TGG GAC AGG TGC CGG GAC CGA TCT GGG TCA TTT TCG GCG AGG          945
Ser Trp Asp Arg Cys Arg Asp Arg Ser Gly Ser Phe Ser Ala Arg
                    305                 310                 315

ACC GCT TTC GCT GGA CGG CGA CGA GGA TCG GCC TGT CGC TTG CGT          990
Thr Ala PHe Ala Gly Ala Arg Arg Gly Ser Ala Cys Arg Leu Arg
                    320                 325                 330

ATT CGG AAT CTT GCA CGC CCT CGT CGG AGT GTG ATG ACA CTG GTT         1035
Ile Arg Asp Leu Ala Arg Pro Arg Arg Ser Val Met Thr Leu Val
                    335                 340                 345

CGC TGT CCG TGC ACC TGG AAC TCC GTA TGT TCT GTC CAA GTT CCT         1080
Arg Cys Pro Cys Thr Trp Asp Ser Val Cys Ser Val Gln Val Pro
                    350                 355                 360

GCT ATC GGC TTG TTC TTA AAT GCC TGT GAG AGT AGT ACA CTG TAC         1125
Ala Ile Gly Leu PHe Leu Asp Ala Cys Glu Ser Ser Thr Leu Tyr
                    365                 370                 375

TGT GA                                                              1130
Cys
```

(2) INFORMATION FOR SEQ ID NO:2:

(i) SEQUENCE CHARACTERISTICS:
        (A) LENGTH: 262
        (B) TYPE: nucleotides
        (C) STRANDEDNESS: Single
        (D) TOPOLOGY: Linear (ii) MOLECULE TYPE:
        (A) DESCRIPTION: cDNA (iii) HYPOTHETICAL: No (iv) ANTI-SENSE: No (vi) ORIGINAL SOURCE:
        (A) ORGANISM: Bovine
        (B) STRAIN:
        (C) INDIVIDUAL ISOLATE: ATC5
        (G) CELL TYPE: mammary gland (ix) FEATURE:
        (A) NAME/KEY: ATC5 3' end
        (B) LOCATION: bovine mammary gland cDNA
            and encoded polypeptide
        (C) IDENTIFICATION METHOD: Sequencing
        (D) OTHER INFORMATION: Encodes a portion of
            acetyl coenzyme A synthetase (xi) SEQUENCE DESCRIPTION: SEQ ID NO:2:

```
TTTCTTAGAC  GTCAGGTGGC  ACTTTTTGGG  GAAATGTGCG  CGGAACCCCT     50

ATTTGTTTAT  TTTTCTAAAT  ACATTCAAAT  ATGTATCCGC  TCATGAGACA    100

ATAACCCTGA  TAAATGCTTC  AATAATATTG  AAAAAGCAAG  AGTATGAGTA    150

TTCAACATTT  CCGTGTCGCC  TTATTCCTTT  TTTGCGGCAT  TTTGCTTCCT    200

GTTTTTTGTA  CGCCTATTTT  TATAGGTTAA  TNTCATGATA  ATAATGGTTT    250

CTTAAGACGT  CA                                                262
```

(2) INFORMATION FOR SEQ ID NO:3:

(i) SEQUENCE CHARACTERISTICS:
        (A) LENGTH: 161
        (B) TYPE: nucleotides
        (C) STRANDEDNESS: Single

```
        (D) TOPOLOGY:  Linear (ii) MOLECULE TYPE:
         (A) DESCRIPTION: cDNA (iii) HYPOTHETICAL:  No (iv) ANTI-SENSE:  No (vi) ORIGINAL SOURCE:
         (A) ORGANISM:  Bovine
         (B) STRAIN:
         (C) INDIVIDUAL ISOLATE:  AR8
         (G) CELL TYPE:  mammary gland (ix) FEATURE:
         (A) NAME/KEY:  DNA of bovine mammary gland
         (B) LOCATION:  bovine mammary gland
         (C) IDENTIFICATION METHOD:  Sequencing
         (D) OTHER INFORMATION:  Encodes a portion of
             acetyl coenzyme A synthetase (xi) SEQUENCE DESCRIPTION: SEQ ID NO:3:

CCGTTGCTGT CGCGCACCAC GCACGCAGCA CACGGCCCCG                              40

CACACAGCCC CATCTTACCC ACCCTGCAAC CAACCCCCGT                              80

CGACTGCCTT ACACACCCGC CCCCGCCGTC CGCCAGCACG                             120

GGGGTGAGAA CAAGGCACTA GGTCGGCCGG CCAGCGCGAC                             160

A                                                                      161

(2) INFORMATION FOR SEQ ID NO:4:

(i) SEQUENCE CHARACTERISTICS:
         (A) LENGTH:  228
         (B) TYPE:  nucleotides
         (C) STRANDEDNESS:  Single
         (D) TOPOLOGY:  Linear (ii) MOLECULE TYPE:
         (A) DESCRIPTION: cDNA (iii) HYPOTHETICAL:  No (iv) ANTI-SENSE:  No (vi) ORIGINAL SOURCE:
         (A) ORGANISM:  Bovine
         (B) STRAIN:
         (C) INDIVIDUAL ISOLATE:  AR8
         (G) CELL TYPE:  mammary gland (ix) FEATURE:
         (A) NAME/KEY:  DNA of bovine mammary gland
         (B) LOCATION:  bovine mammary gland
         (C) IDENTIFICATION METHOD:  Sequencing
         (D) OTHER INFORMATION:  Encodes a portion of
             acetyl coenzyme A synthetase (xi) SEQUENCE DESCRIPTION: SEQ ID NO:4:

TGCAGGTCGA CTCTAGAGGA TCCCGGGTAC CGAGCTCGAA                              40

TTCCGTTGCT GTCGCCGTTG CTGTCGCGCT GGCCGGCCGA                              80

CCTAGTGCCT TGTTCTCACC CCCGTGCTGG CGGACGGACG                             120

CCGCGCGGGG GCGGGTGTGT AAGGCAGTCG ACGCGGGGGT                             160

TGGTTGCAGG GTGGGTAAGA TGGGGCTGTG TGCGGGGCCG                             200

TGTGCGTGCG TGCGTGCGTG CCGGACAC                                          228

(2) INFORMATION FOR SEQ ID NO:5:
```

```
    (i) SEQUENCE CHARACTERISTICS:
        (A) LENGTH:  16
        (B) TYPE:  nucleotides
        (C) STRANDEDNESS:  Single
        (D) TOPOLOGY:  Linear (ii) MOLECULE TYPE:
        (A) DESCRIPTION: synthetic DNA (iii) HYPOTHETICAL:  No (iv) ANTI-SENSE:  No (vi) ORIGINAL SOURCE:
        (A) ORGANISM:
        (B) STRAIN:
        (C) INDIVIDUAL ISOLATE:
        (G) CELL TYPE:

(ix) FEATURE:
        (A) NAME/KEY:  ECOR1 adaptor
        (B) LOCATION:
        (C) IDENTIFICATION METHOD:
        (D) OTHER INFORMATION:

(xi) SEQUENCE DESCRIPTION: SEQ ID NO:5:

AATTCCGTTG CTGTCG                                                    16

(2) INFORMATION FOR SEQ ID NO:6:

(i) SEQUENCE CHARACTERISTICS:
        (A) LENGTH:  12
        (B) TYPE:  nucleotides
        (C) STRANDEDNESS:  Single
        (D) TOPOLOGY:  Linear (ii) MOLECULE TYPE:
        (A) DESCRIPTION: synthetic DNA (iii) HYPOTHETICAL:  No (iv) ANTI-SENSE:  No (vi) ORIGINAL SOURCE:
        (A) ORGANISM:
        (B) STRAIN:
        (C) INDIVIDUAL ISOLATE:
        (G) CELL TYPE:

(ix) FEATURE:
        (A) NAME/KEY:  EcoR1 adaptor
        (B) LOCATION:
        (C) IDENTIFICATION METHOD:
        (D) OTHER INFORMATION:

(xi) SEQUENCE DESCRIPTION: SEQ ID NO:6:

GGCAACGACA GC                                                        12

(2) INFORMATION FOR SEQ ID NO:7:

(i) SEQUENCE CHARACTERISTICS:
        (A) LENGTH:  17
        (B) TYPE:  nucleotides
        (C) STRANDEDNESS:  Single
        (D) TOPOLOGY:  Linear (ii) MOLECULE TYPE:
        (A) DESCRIPTION: Synthetic DNA (iii) HYPOTHETICAL:  No (iv) ANTI-SENSE:  No (vi) ORIGINAL SOURCE:
        (A) ORGANISM:  Bovine
        (B) STRAIN:
```

```
        (C) INDIVIDUAL ISOLATE:
        (G) CELL TYPE:

(ix) FEATURE:
        (A) NAME/KEY:  primer
        (B) LOCATION:
        (C) IDENTIFICATION METHOD:
        (D) OTHER INFORMATION:

(xi) SEQUENCE DESCRIPTION: SEQ ID NO:7:

GTTTTCCCAG TCACGAC                                                  17

(2) INFORMATION FOR SEQ ID NO:8:

(i) SEQUENCE CHARACTERISTICS:
        (A) LENGTH:  17
        (B) TYPE:  nucleotides
        (C) STRANDEDNESS:  Single
        (D) TOPOLOGY:  Linear (ii) MOLECULE TYPE:
        (A) DESCRIPTION: synthetic DNA (iii) HYPOTHETICAL:  No (iv) ANTI-SENSE:  No (vi) ORIGINAL SOURCE:
        (A) ORGANISM:
        (B) STRAIN:
        (C) INDIVIDUAL ISOLATE:
        (G) CELL TYPE:

(ix) FEATURE:
        (A) NAME/KEY:  primer
        (B) LOCATION:
        (C) IDENTIFICATION METHOD:
        (D) OTHER INFORMATION:

(xi) SEQUENCE DESCRIPTION: SEQ ID NO:8:

CAGGAAACAG CTATGAC                                                  17
```

SELECTION METHOD INVOLVING ACETAL COENZYME A SYNTHETASE IN CALVES

This is a divisional of copending application(s) Ser. No. 08/613,965 filed on Mar. 8, 1996.

BACKGROUND OF THE INVENTION (1) Field of the Invention pUC19-AR8 was deposited with the American Type Culture Collection Under the Budapest Treaty on Aug. 7, 1997 as ATCC 209191. pUC19-pATC5 was deposited with the American Type Culture Collection Under the Budapest Treaty on Mar. 25, 1996 as ATCC 98008. All restrictions on the distribution of these deposits of pUC19-pATC5 and pUC19-AR8 are irrevocably removed on granting of a patent on this application and the deposit will be replaced if viable samples cannot be dispensed by the depository as required. The address of the American Type Culture Collection is 12301 Parklawn Drive, Rockville, Md. 20852.

(2) Description of Related Art

Molecular mechanisms regulating utilization of substrates in ruminants are not known. The regulation of acetate for milk synthesis at the molecular level is known to be important. Acetate as acetyl coenzyme A (acetyl-CoA) is a major substrate for milk synthesis and occupies a central position in metabolism of Holstein mammary gland as well as in both prokaryotic and eukaryotic cells. Acetyl-CoA is generated via the acetate activation reaction catalyzed by acetyl coenzyme A synthetase (ACS).

The expression of ACS activity in ruminants is unique. ACS activity is constitutive in heart, controlled by nutrition and physiological state in the mammary gland, but not expressed in liver (Mellenberger, B. W., et al., Biochem. J. 136:741 (1973); Marinez, D. I., et al., J. Agric. Food Chem. 24:927 (1976); Ricks, C. A. and R. M. Cook, J. Dairy Sci. 64:2324 (1981)). Ruminant liver is not lipogenic (Emery, R. S., Mobilization, turnover, and disposition of adipose tissue lipids. IN: *Digestive physiology and metabolism in ruminants.* Ruckebusch, Y. and P. Thivend (eds.) Avi Publ. Co., Westport, Connecticut, p. 541 (1980)). Therefore, acetate is not utilized by liver. The liver utilizes propionate as the major source of glucose (Reynolds, C. K. et al., J. Dairy Sci. 71:2395 (1988); Amaral, D. M. et al., J. Dairy Sci. 73:1244 (1990)). Since there is a paucity of glucose in ruminants, this pattern of tissue utilization of acetate spares glucose for other vital metabolic functions (Ricks, C. A. and R. M. Cook, J. Dairy Sci. 64:2324 (1981)). ACS is the first committed step in acetate oxidation which is a major source of energy for milk synthesis. Also, in the ruminant mammary gland, ACS is the first committed step in fatty acid synthesis. The activity of ACS is marginal in a dry gland, increases to peak lactation, and then declines in activity as lactation advances (Marinez, D. E., et al., J. Agric. Food Chem. 24:927 (1976)).

In early lactation, blood growth hormone is relatively high and insulin is low. As lactation advances and milk production declines, blood levels of growth hormone decreases and insulin increases. Also, high producing cows have lower blood insulin and higher growth hormone than do low producing cows (Ghirardi, G. G. and R. M. Cook, J. Dairy Sci. 770:(Suppl. 1):49 (Abstr.) (1987)). Insulin inhibits and growth hormone stimulates ACS activity in lactating goat mammary gland. As lactation advances, ACS activity decreases sharply but can be partially reinstated by injecting a combination of growth hormone, prolactin, and dexamethasone (Marinez, D. I., et al., J. Agric. Food Chem. 24:927 (1976)). ACS activity is directly correlated with milk production. Thus, as lactation advances, less acetate can be utilized. There is a need for identification of cows which may be in need of treatment to augment lactation.

U.S. Pat. No. 5,041,371 to Cowan et al describes an assay and test kit which uses a DNA probe to label a gene encoding a modification of genes adjacent to the gene encoding bovine prolactin which is a protein important to milk production. This method is focused on the presence or absence of the gene and not on the level of expression of the protein. The gene in question is within 1.5 kb of the bovine prolactin gene. Bulls and daughters of bulls are tested for breeding purposes. This method and test kit is marketed commercially.

SUMMARY OF INVENTION

The present invention relates to a method for determining potential for milk production of a bovine which comprises: determining a level of acetyl coenzyme A synthetase (ACS) from mammary tissue; and estimating the milk production potential of the bovine based upon the ACS.

The present invention relates to a method for assaying for the presence of a bovine gene of a bovine to determine potential for milk production which comprises: providing a first genetic material selected from the group consisting of DNA and mRNA derived from mammary gland tissue of the bovine: binding the first genetic material with a second labeled genetic material selected from the group consisting of DNA and mRNA encoding a unique region of acetyl coenzyme A synthetase (ACS) as a probe to determine an amount of the ACS in the tissue; and estimating the milk producing potential of the bovine.

The present invention relates to a method for determining potential for milk production in a population of bovines for breeding purposes which comprises: determining a level of acetyl coenzyme A synthetase (ACS) from mammary tissue in the population; estimating the milk production potential of the bovines in the population based upon the ACS; and selecting the bovines from the population for breeding for milk production.

The present invention relates to a method for assaying for the presence of a bovine gene in a population of bovines to determine milk production for breeding purposes which comprises for each bovine: providing a first genetic material selected from the group consisting of DNA and mRNA derived from mammary gland tissue from the population of bovines: binding the first genetic material with a second labeled genetic material selected from the group consisting of DNA and mRNA encoding a unique region of acetyl coenzyme A synthetase (ACS) as a probe to determine an amount of the ACS in the tissue; estimating the milk producing potential of the bovines; and selecting the bovines from the population for breeding for milk production.

The method can be used for binding the ACS with selective binding material, particularly and antibody or multiple antibodies. The binding material is labeled for detection by a radioactive, chemiluminescent, fluorescent, chemically reactive, such as enzyme, or the like label as is well known.

Preferably the level of ACS is determined using a probe which is selective for mRNA of mammary cells. This preferred method is for assaying for the presence of a bovine gene of a bovine to determine potential for milk production which comprises: providing a first genetic material selected from the group consisting of DNA and mRNA derived from mammary gland tissue of the bovine: binding the first genetic material with a second labeled genetic material selected from the group consisting of DNA and mRNA encoding a unique region of acetyl coenzyme A synthetase (ACS) as a probe to determine an amount of the ACS in the tissue; and estimating the milk producing potential of the bovine. The probe is preferably a cDNA which is labeled. The label can be any of the same types of labels discussed above.

pUC19-AR8 was deposited with the American Type Culture Collection Under the Budapest Treaty on Aug. 7, 1997 as ATCC 209191. pUC19-pATC5 was deposited with the American Type Culture Collection Under the Budapest Treaty on Mar. 25, 1996 as ATCC 98008. All restrictions on the distribution of these deposits of pUC19-pATC5 and pUC19-AR8 are irrevocably removed on granting of a patent on this application and the deposit will be replaced if viable samples cannot be dispensed by the depository as required. The address of the American Type Culture Collection is 12301 Parklawn Drive, Rockville, Md. 20852.

The present invention also relates to a kit for assaying for the presence of a bovine gene in a population of bovines to determine potential for milk production for breeding purposes which comprises in separate containers: a probe which is a first genetic material selected from the group consisting of DNA and RNA encoding a unique region of acetyl coenzyme A synthetase (ACS); a second bovine genetic material selected from the group consisting of DNA and RNA containing the region ACS which binds to the probe to serve as a control. The second bovine genetic material serves a positive control for the accuracy of the results of the use of the test kit.

In one embodiment, the mRNA of the mammary gland can be isolated, separated such as by electrophoresis and then probed to determine the level of ACS. The level of the ACS is a function of the amount of the mRNA.

The method for bovine population selection involves less cost because fewer animals have to be bred. In particular, daughters are tested as calves before milk production to determine levels of ACS production. Animals with a poor production potential for ACS are removed from breeding. Elite breeding lines are developed using ACS for population selection for milk production along with other normal breeding criteria, particularly lineage. Over time substantial improvements in milk production are achieved.

There are several chemical methods available to regulate the rumen ecosystem such that end-products of feed fermentation can be altered to better support growth and fattening or milk production which can be monitored using the method of the present invention. A knowledge of the mechanism of action of these chemicals at the molecular level provides new and better methods to regulate the rumen ecosystem. However, this is just one aspect of improving feed utilization by ruminants. A knowledge of utilization of rumen fermentation products by extrarumional tissue is paramount if improved efficiency in food producing animals is to be achieved. This will require detailed knowledge of the regulation of genes important in substrate utilization. Also, the availability of probes for ACS provides opportunities for genetic modification of ruminants using marker assisted selection programs.

OBJECTS

It is therefore an object of the present invention to provide test kits and assay methods for determining potential for milk production. Further, it is an object of the present invention to (1) provide DNA's which can be used as probes; and (2) which can be used in microorganisms to express the ACS. Further still, it is an object of the present invention to provide a method and test kit which is simple to use, inexpensive and reliable for estimating potential for milk production. These and other objects will become increasingly apparent by reference to the following description and the drawings.

BRIEF DESCRIPTION OF DRAWINGS

FIG. 7 is a photograph showing isolation of λgt11-AR8 cDNA fragment. λgt11-AR8 DNA was purified with PEG and centrifuged using a glycerol gradient. The DNA was digested with EcoRI and separated in agarose gel. The inset shows DNA marker (lane 1) and digested λgt11-AR8 (lanes 2, 3 and 4).

FIG. 8 is a photograph showing a Southern blot of N. crassa acetyl-CoA synthetase gene probed with $\alpha^{32}$P-AR8. The fungal clone was digested with HindIII. DNA was separated in agarose gel. The results indicates that AR8 is homologous to the fungal acetyl-CoA synthetase gene.

FIG. 9 is a photograph showing a Southern blot of bovine genomic DNA probed with $\alpha^{32}$P-AR8. Bovine genomic DNA was digested with EcoRI. DNA was separated in agarose gel. The results indicate one gene copy of acetyl-CoA synthetase.

FIGS. 12A and 12B show nucleotide acid sequences of AR8. AR8 was sequenced in both directions FIGS. 12A and 12B (SEQ ID NO:3 and SEQ ID NO:4, respectively) showing partial sequences of AR8.

FIGS. 19A and 19B are a photographs of the effect of stage of lactation on relative levels of acetyl-CoA synthetase poly(A$^+$) RNA in Holstein mammary gland. Mammary gland poly(A$^+$)RNA was isolated from dry, 60, 120 and 180 day lactating Holstein. Five λg of the mammary poly(A$^+$) RNA were spotted on nylon filter and probed with $\alpha^{32}$p-AT5. Acetyl-CoA synthetase mRNA level was highest at 120 days of lactation. In panel A, columns 1, 2, 3 and 4 represent samples from cows 60, 120, 180 days postpartum and dry mammary gland respectively. β-actin hybridization is shown in panel B.

FIG. 20 is a photograph of a Western blot analysis of mitochondrial extract, examined with rabbit anti-bovine acetyl-CoA synthetase gamma globulin. Mitochondrial proteins were separated in 12.5% SDS-polyacrylamide gel. Alkaline phosphatase-conjugated goat anti-rabbit IgG was used as second antibody. 20 λg of protein was used for each extract. lanes: 1, heart; 2, liver; 3, mammary gland; 4, kidney; and 5, spleen. The acetyl-CoA synthetase antibody used in this experiment appears to have a great deal of non-specific reactivity to other proteins.

FIGS. 26A-1 and 26A-2 are a nucleotide and predicted amino acid sequence of ATC5 (Seq ID NO:1). ATC5 was sequenced in one direction. The nucleotide sequence (FIG. 26A) was derived from sequencing one strand. The EcoRI site is of nucleotide 215(M). FIG. 26B is a nucleic acid sequence of ATC5 3' end (Seq ID No:2).

DESCRIPTION OF PREFERRED EMBODIMENTS

Figure 1:
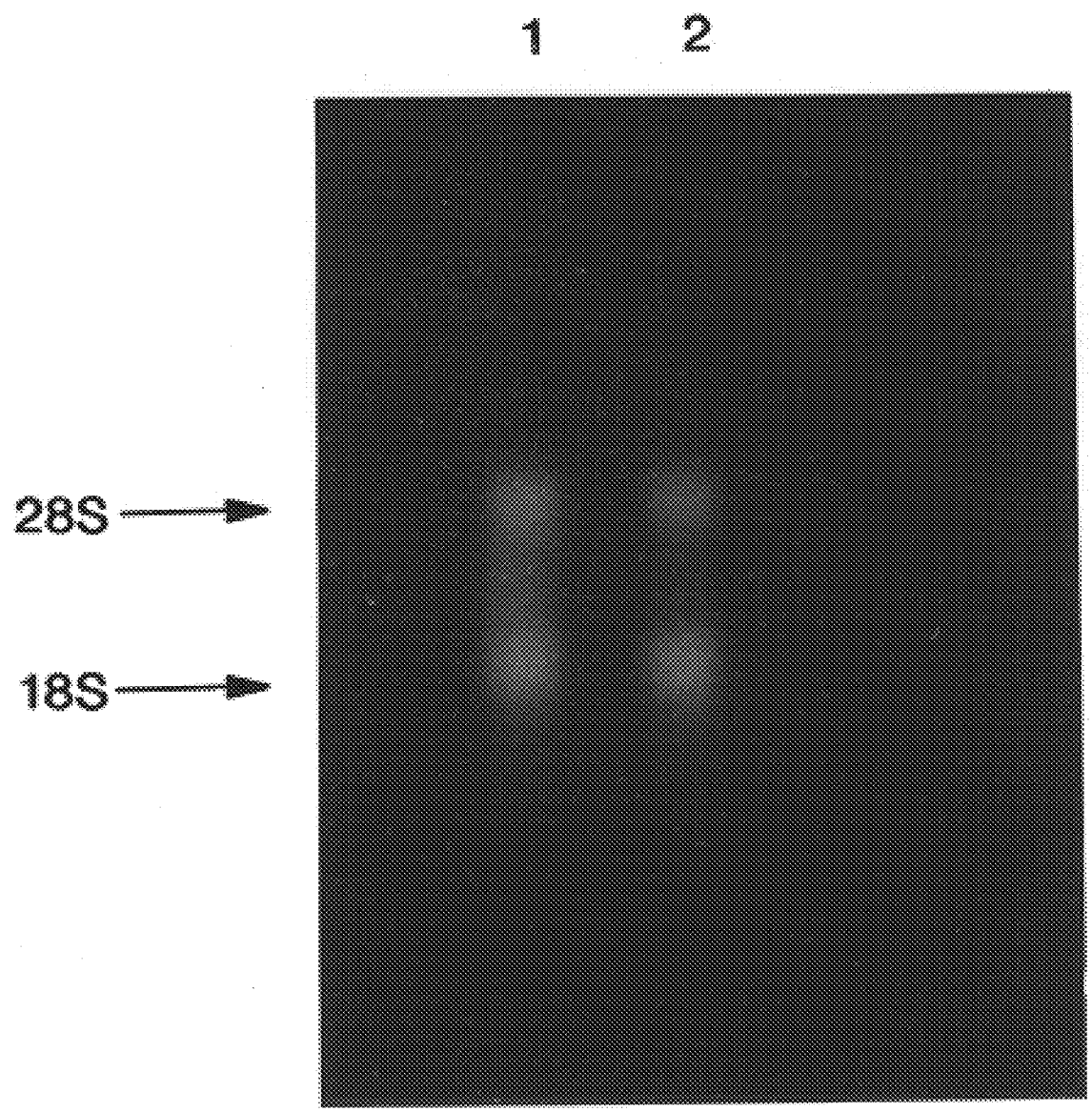
FIG. 1 is a photograph showing formaldehyde gel electrophoresis of total mammary gland RNA isolated from a Holstein cow 60 days postpartum. Each Lane contains 20 μg of total RNA.

In general, cDNA cloning of the ACS gene was initiated using poly(A$^+$)RNA isolated from bovine mammary tissue, taken at peak lactation. Mammary gland mRNA was reversed transcribed with AMV reverse transcriptase (Promega Inc., Madison, Wis.). cDNA's produced were cloned into the EcoRI site of lambda gt11. Initial screening with rabbit anti-ACS sera, prepared by injection of purified bovine ACS, yielded a truncated cDNA clone, AR8. AR8 remained positive through several rounds of plaque purification. Subsequent screening of 750,000 plagues using AR8 yielded 1 clone, designated ATC5, which remained positive through several rounds of plaque purification. ATC5 contains a 4.2 Kbp insert, more than sufficient to encode the complete ACS protein. The insert from ATC5 was excised by EcoRI digestion and subcloned into the EcoRI site of pUC19 (generating pATC5) for further analysis and sequencing.

Prior to initiation of full-scale DNA sequence analysis, several steps were taken to ensure pATC5 represented a true copy of ACS gene coding sequences:

1. Rabbit anti-ACS, was affinity purified using the fusion protein produced by induction of pATC5 with IPTG. Purified anti-ACS removed over 90% of ACS activity from a preparation of partially purified bovine mammary ACS. In contrast, preimmune sera did not adversely affect ACS activity.

2. Anti-ACS, affinity purified using LacZ-ACS fusion protein from clone pAR8 was used in western blots of mitochondrial extracts from heart, liver, kidney, mammary gland and spleen. Proteins with the expected molecular weight and tissue distribution as ACS were recognized.

3. Preliminary DNA sequencing of AR8 and pATC5 revealed an open reading frame with 25% homology to other synthetases (ATP and HSCoA binding proteins). No homology to common structural proteins was observed.

4. The pattern of RNA expression detected in bovine tissues is consistent with known protein expression patterns of ACS. Specifically, heart and mammary gland contain significant amounts of ACS RNA while liver and kidney contain very little.

A restriction map of the 4.2 Kbp insert of pATC5 has been prepared and the insert partially sequenced (SEQ ID NO:1). The cDNA was sequenced, revealing a single long open reading frame. Northern blots of poly(A+) RNA from bovine heart, liver, mammary gland, and kidney were probed with (alpha-$^{32}$P)-ATC5. Northern analyses clearly show multiple forms of ACS mRNA in most tissues. For example, 3 distinct transcripts were detected in heart and mammary gland while 2 transcripts were detected in kidney and 1 in liver. ACS transcripts range in size from 08 to 5.2 kb. Multiple forms of ACS mRNA were not unexpected, based on results from other synthetases, and may be the result of multiple promoters and/or alternative splicing. It is curious, however, that a faint ACS mRNA (4.2 kb) would be present in liver where no ACS activity can be detected. This suggests that either the liver transcript is not translated, leads to translation of an inactive molecule, or is regulated at the post-translational level. It is also possible that ACS probe ATC5 hybridized with another closely related mRNA (i.e. propionyl CoA synthetase) in the liver.

Multiple forms of ACS mRNA, acetyl-CoA synthetase could be regulated by tissue specific promoters. This would explain why the enzyme is active in heart (3 forms of mRNA) but not liver (1 form of mRNA). Also, there may be an alternative promoter in the mammary gland that is activated by nutrition and/or physiological state. However, tissue specific alternative splicing mechanisms for acyl-CoA synthetases that produce protein isoforms specific for individual fatty acids cannot be ruled out at this point. Understanding regulation of ACS is important because the reaction catalyzed by this enzyme is the initial step in fatty acid synthesis and acetate oxidation in ruminants.

EXAMPLE 1

A complementary DNA (cDNA) of 4200 base pairs expressing the bovine ACS was isolated by screening a bovine cDNA library with polyclonal antibody produced against the purified protein. Partial sequence analysis revealed an open reading frame of 969 nucleotides corresponding to 323 amino acids. The DNA sequence obtained displayed 42% homology to the *N. crassa* ACS gene. Neither the DNA nor the protein sequence showed significant similarity to other currently published sequences. The isolated cDNA was expressed in bacteria to yield a catalytically active enzyme. Specific activity of the crude lysate obtained exceeded that of the wild type vector crude lysate by a factor of 2. Using cloned ACS as probe, highest level of ACS mRNA in the mammary gland was found at 120 days postpartum. Southern analysis of bovine genomic DNA suggests that the ACS gene has a single copy per haploid genome. Immunoblot analysis and enzyme assay studies suggest that the rabbit anti-bovine ACS has a high affinity for ACS. The ACS gene is expressed in heart, kidney, and mammary gland but not in liver as judged by northern and western blot analysis. In vitro transcription\translation products of the cloned ACS gene (55 kD) is 8 kD smaller than the native protein. This difference is most probably due to lack of glycosylation in the in vitro translation system. Northern blots probed with the ACS cDNA showed more than one mRNA species, suggesting that alternative splicing and/or multiple promoter(s) may exist for the ACS gene. Alternative regulation mechanisms for ACS gene were proposed to explain ACS mRNA multiple forms and tissue specific expression.

MATERIALS AND METHODS

Extraction of Cow Mammary Gland Total RNA

To avoid the accidental introduction of trace amounts of RNases from potential sources in the laboratory, a number of precautions were used. All glassware was made RNase free by baking at 180° C. overnight (at least 12 hr). Sterile, disposable plastic ware, which are RNase free, was used for the preparation and storage of the RNA without pretreatment. The ultra pure water and all reagents (except the ones containing Tris) were treated with 0.1% diethyl pyrocarbonate (DEPC) and sterilized by autoclaving, to insure that they also were RNase free. All solutions and buffers were prepared by using RNase free glassware, and DEPC treated water. Also, a set of chemicals was reserved for work with RNA only (handled with baked spatulas). RNA's were kept on ice at every step except during resuspension of pellets and during column chromatography, both of which were done at room temperature (R.T.=23–25° C.).

RNA was isolated from frozen (–80° C.) mammary gland tissue by the guanidinium-isothiocyanate cesium chloride procedure described by Glisin et al (Biochemistry. 13:2633 (1974)) and Ullrich et al. (Science. 196:1313 (1977)). All glassware tubes and reagents were RNase free. Briefly, 4 grams of mammary gland tissue were broken into small pieces under liquid nitrogen and homogenized in 40 ml of homogenization buffer (4 M guanidinium isothio-cyanate, 25 mM Na citrate, pH 7.0, 0.1 M β-mercaptoethanol and 0.5% sarkosyl). To remove the cell debris, the homogenate was centrifuged in sterile centrifuge tubes at 1,500×g for 5 minutes at room temperature. The supernatant was transferred to a sterile tube and DNA sheared by passing the supernatant through an 18 gauge needle 12 times. The supernatant was then centrifuged at 5,000×g at 15° C. for 20 minutes. Twelve ml of the supernatant were then layered on 26.5 ml of 5.7 M cesium chloride and 0.1 M EDTA at pH 7.5 and centrifuged at 126000 g and 20° C. for 24 hours using a Beckman SW28 rotor. The supernatant above the CsCl cushion was removed with a sterile pasteur pipette, then all but one ml of CsCl were removed with a second sterile pipette. The centrifuge tube was cut just above the remaining CsCl using a razor blade. CsCl was removed and the RNA pellet washed with 70% ethanol and dried in a speedvac. The RNA was dissolved in 0.4 ml of TE buffer, pH 7.6, (10 mM Tris-HCl, pH 7.6, 1 mM EDTA) and transferred to a sterile 2 ml microfuge tube. The solution was extracted once with a 1:1 mixture of chloroform and TE saturated-phenol and once with chloroform. RNA was precipitated by adding 40 μl of RNase-free 3 M sodium acetate, pH 5.2, and 1 ml of ice cold ethanol and held at –70° C. for 20 minutes. RNA was collected by centrifuging at 12,000×g for 15 minutes at 4° C. and washed with 70% ethanol and dried for 2 minutes in a speedvac. The RNA pellet was dissolved in 250 μl of TE buffer (pH 7.6) and stored at –70° C. RNA was diluted 100 times with sterile DEPC treated H$_2$O and the concentration measured in a spectrophotometer at 260 nM. RNA formaldehyde gels were run to ensure that was no significant degradation of the RNA samples before isolation of poladenylated RNA.

Formaldehyde Gel Electrophoresis

This method is adopted from those of Lehrach et al. (Biochemistry. 16:4743 (1977)) and Goldberg (Proc. Natl. Acad. Sci. 77:5794 (1980)). RNA was examined on 1.2% agarose-formaldehyde gels. 1.2 g of agarose were dissolved in 71.8 ml H$_2$O and 10 ml of 10×MOPS (1×MOPS is 0.04 M MOPS, pH 7.0, 10 mM Na acetate, 1 mM EDTA) by heating in a microwave oven. The solution was cooled to 60° C. and 17.8 ml of formaldehyde were added. A 11.5×15.5 cm gel was poured and 5 to 25 µg of RNA in 5 µl of TE buffer were mixed with 15 µl of sample buffer (200 µl 10×MOPS, 350 µl formaldehyde, and 1 ml of formamide), and heated at 65° C. for 15 minutes. Then 4 µl of sterile loading buffer were added (50% glycerol, 1 mM EDTA, 0.4% xylene cyanol and 0.4% bromophenol blue). The electrophoresis buffer was 1×MOPS. Electrophoresis was at 100 V for 2–2.5 hours. The gel was stained one hour with a solution of 0.1 M ammonium acetate containing 0.5 µg/ml of ethidium bromide, destained for 30 minutes in 0.1 M ammonium acetate and examined under UV light.

Isolation of Polyadenylated RNA

Polyadenylated Poly(A$^+$) mRNA was isolated from total RNA by using oligo(dT)-cellulose columns (Pharmacia Cat. # 279258) according to manufacturers instructions. The column was washed once with a solution of 0.1 N NaOH and 0.5 mM EDTA then 2 times with 1 ml of equilibration buffer (10 mM Tris-HCl, pH 7.4, 1 mM EDTA, and 0.5 M NaCl). RNA (600 µg) in 1 ml of TE buffer, pH 7.6, was heated at 65° C. for 5 minutes and placed in an ice bath. Then 0.2 ml of high salt buffer (10 mM Tris-HCl, pH 7.4, 1 mM EDTA and 3 M NaCl) were added. One ml was transferred to the oligo(dT)—cellulose column. The column was centrifuged at 350 g for 2 minutes and then washed two times with 0.25 ml of high salt buffer by centrifuging at 350 g for 2 minutes. The column was then washed 3 times with 0.25 ml of equilibration buffer. To isolated poly(A$^+$) RNA the column was eluted 4 times with 250 µl aliquots of TE buffer, pH 7.4, at 65° C. The entire eluate was collected in a RNase-free sterile tube.

Construction of Bovine Mammary gland cDNA Library

First Strand cDNA Synthesis cDNA was synthesized using a Promega kit (Cat. # C2100). The kit uses the procedure introduced by Okayama and Berg (Mol. Cell. Biol. 2:161 (1982)) for the first strand synthesis. Second strand cDNA was synthesized by a modification of Gubler and Hoffman method (Gubler and Hoffman, Gene. 25:263 (1983)). Parallel reactions were performed during both first and second strand synthesis reactions so that mass yields could be determined by labeling either the first strand or second strand.

Avian myeloblastosis virus (AMV) reverse transcriptase was diluted 10 fold with a solution containing 10 mM potassium phosphate, pH 7.4, 0.2% Triton X-100, 2 mM dithiothreitol (DTT), and 10% glycerol, and kept on ice 30 minutes before initiating the reaction. Five µg of poly(A$^+$) RNA were annealed to 2.5 µg of oligo dT$_{15}$ primer by heating at 70° C. for 5 minutes then cooled to room temperature. Five µl of a solution containing 250 mM Tris-HCl, pH 8.3, 250 mM KCl, 50 mM Mg Cl$_2$, 2.5 mM spermidine, 50 mM DTT, 5 mM each of dATP, dCTP, dGTP, and dTTP were added followed by 25 units of RNasin (ribonuclease inhibitor), 2.5 µl of 40 mM sodium pyrophosphate (preheated to 70° C.), 75 units of AMV reverse transcriptase, and sterile DEPC treated water to a final volume of 25 µl. The reaction was carried out at 42° C. for 60 minutes and stopped by placing the tubes on ice. To follow first strand synthesis, 5 µl of the reaction mixture were incubated with 5 µCi of [α$^{32}$P] dCTP. Ninety-four µl of 50 mM EDTA were added to the tube containing α$^{32}$P. This solution was passed through Sephadex G-50 to remove [α$^{32}$P]dCTP and checked for first strand synthetase using alkaline gel electrophoresis and autoradiography.

Second Strand cDNA synthesis

The second strand of cDNA was synthesized by adding to the reaction mixture 10 µl of a solution containing 500 mM Tris-HCl, pH 7.2, 900 mM KCl, 30 mM Mg Cl$_2$, 30 mM DTT, and 0.5 mg/ml of BSA followed by 23 units of E. coli polymerase 1, 0.8 units of E. coli RNase H and sterile DEPC treated water to a final volume of 100 µl. The reaction was carried out at 14° C. for 4 hours. To follow second strand synthesis, 10 µl of the reaction mixture were transferred to a tube containing 5 µCi of [α$^{32}$P] dCTP and incubated as above. Ninety µl of 50 mM EDTA were then added to the tube containing $^{32}$P and this reaction mixture was examined for second strand synthesis.

T4 Polymerase Blunting of cDNA

To produce cDNA with blunt ends, the double stranded cDNA was then heated at 70° C. for 10 minutes and centrifuged briefly in a microfuge for 4 seconds at 12,000×g at room temperature, and then incubated at 37° C. for 10 minutes in the presence of 10 units of T$_4$ DNA polymerase. The reaction was stopped by placing the reaction mixture on ice and adding 10 µl of 200 mM EDTA. The reaction mixture was extracted with an equal volume of a 1:1 mixture of chloroform and phenol equilibrated with TE buffer followed by extraction with chloroform. The cDNA was precipitated from the aqueous phase by adding 0.1 volumes of 2.5 M sodium acetate (pH 5.2) and 2.5 volumes of ice-cold ethanol and allowed to stand 2 hours at −20° C. followed by centrifuging 15 minutes at 4° C. The cDNA pellet was washed with 70% cold ethanol, dried in a speedvac, dissolved in TE buffer, pH 7.6, and the yield measured at 260 nm using a spectrophotometer.

Alkaline Gel Electrophoresis

Alkaline agarose gels (McDonell et al., J. Mol. Biol. 110:119 (1977)) are used to check the size of the first and second strands of cDNA synthesized by reverse transcriptase. 0.9% agarose solution was prepared in water and cooled to 60° C. NaOH was added to a final concentration of 50 mM and EDTA to 1 mM and the solution poured in the gel casset (12×15 cm). After the solution solidified the comb was removed and the gel covered with 1× alkaline buffer (50 mM NaOH, 1 mM EDTA, pH 8.0). The DNA sample (100 µl) was precipitated and dissolved in a solution containing 20 µl of 50 mM NaOH, and 1 mM EDTA. Then 4 µl of sample loading buffer (60 mM NaOH, 1.2 mM EDTA, 3.6% ficoll 400, 0.03% bromophenol green, 0.05% xylene cyanol FF) were added to the DNA. The DNA was placed in the wells (0.5 cm in width) and electrophoresis (50 V) was carried out until the dye had migrated approximately two thirds of the length of the gel. The gel was removed and placed in 7% trichloroacetic acid (TCA) for 30 minutes at room temperature and then dried overnight under several layers of paper towels. The dried gel was wrapped in Saran Wrap and examined using autoradiography at −70° C.

Ligation of EcoRI Adaptors to Double Stranded cDNA

Small cDNA fragments were removed using Sephacryl S-400. The reaction mixture to ligate EcoRI adaptors to the cDNA was 3 µl of 10× ligase buffer (1× ligase buffer is 30 mM Tris-HCl, pH 7.8, 10 mM Mg Cl$_2$, 10 mM DTT and 1 mM ATP), 3 µl BSA (1 mg/ml), 1 µl of cDNA (234 ng), 1 µl of a solution containing 1 pmol of EcoRI adaptors (5'AATTCCGTTGCTGTCG3' (SEQ ID NO:5)

3'GGCAACGACAGC5'), (SEQ ID NO:6) 7.5 Weiss units (Weiss et al., J. Biol. Chem. 243:4543 (1968)) of T$_4$ DNA ligase (1.5 µl), and sterile deionized H$_2$O to a final volume of 30 µl. The reaction was carried out for 18 hours at 15° C. followed by heating at 70° C. for 10 minutes. The reaction mixture was cooled to room temperature. To phosphorylate the 5' end of the EcoRI adaptors, the following was added to the reaction mixture: 4 μl of a solution containing 700 mM Tris-HCl, pH 7.6, 100 mM Mg Cl$_2$, and 50 mM DTT, 2 μl of ATP (0.2 nM), 10 units of T$_4$ polynucleotide kinase, and sterile deionized H$_2$O to a final volume of 40 μl. The reaction was carried out at 37° C. for 30 minutes, then 60 μl of TE buffer, pH 7.6, were added and the reaction mixture was extracted one time with a 1:1 mixture of chloroform and phenol equilibrated with TE buffer and one time with chloroform. Unligated EcoRl adaptors were removed by using Sephacryl S-400 column. The cDNA was precipitated with Na acetate cold ethanol, washed with 70% ethanol, dried in speedvac and dissolved in 5 μl of TE buffer, pH 7.6.

Ligation of cDNA into λgt11

Sephacryl-400 purified cDNA was ligated into the EcoRI site of λgt11 (Young, R. A. and R. W. Davis, Proc. Natl. Acad. Sci. 80:1194 (1983); and Young, R. A. and R. W. Davis, Science. 222:778 (1983)) the reaction mixture contained 2 μl of a solution of 300 mM Tris-HCl, pH 7.8, 100 mM Mg Cl$_2$, 100 mM DTT, 10 mM ATP, 1 μl of cDNA, 1 μl of EcoRI cut, dephosphorylated λgt11 DNA (0.5 μg), 1 Weiss unit of T$_4$ DNA ligase and sterile deionized water to a final volume of 10 μl. The reaction was carried out at 22° C. for 3 hours. Fifty μl of Packgene extract (Promega Cat. # K3154) were added and the solution incubated for 2 hours at 22° C. A solution containing 20 mM Tris-HCl, pH 7.4, 100 mM NaCl, and 10 mM Mg SO$_4$ and 25 μl of chloroform were added. The packaged DNA was stored at 4° C.

Titration of cDNA library

The titer of λgt11 phage was determined by standard procedures using $E.$ $coli$ Y1090rk$^-$ (Promega packgene kit). To demonstrate recombinant phage, 100 μl of diluted ($10^2$–$10^7$) λgt11 were incubated with 100 μl (2×10$^8$ cells) of $E.$ $coli$ Y1090rk$^-$ for 20 minutes at 37° C. The phage-infected $E.$ $coli$ were added to 4 ml of sterile top agarose (10 g bacto tryptone, 5 g bacto yeast extract, 10 g NaCl, and 8 g of agarose in 1 liter of deionized H$_2$O) which contained 4 μl ampicillin (50 μg/ml of H$_2$O), 40 μl of 100 mM isopropyl β-D-thiogalactopyranoside (IPTG) in H$_2$O, 40 μl of 2% 5-bromo-4-chloro-3-indolyl-β-D-galactopyranoside (X-Gal) in dimethyl-formamide. The top agarose at 50° C. was layered onto a 90 mm Petri dish containing 25 ml of low-agar-ampicillin (10 g bacto tryptone, 5 g bacto yeast extract, 15 g bacto agar, and 5 g NaCl per liter of deionized water which was autoclaved and cooled to 50° C. before adding ampicillin at 50 μg/ml). The plates were incubated overnight at 37° C. Each agar plate had about the same number of clear and blue-colored plaques indicating that about 50% of the plaque forming units were recombinant, as expected.

cDNA Library Amplification

The library was amplified by the plate lysate method using the restriction minus host Y1090rk$^-$. Recombinant λgt11 phage library in $E.$ $coli$ Y1090rk$^-$ was plated on 90 mm agar plates at 5×10$^4$ recombinants per plate, and incubated at 43° C. until the plaques appear and merge (9 hours). The plates were cooled to 4° C. and each plate overlayed with 4 ml (SM) buffer (50 mM Tris-HCl, pH 7.5, 100 mM NaCl, 8 mM MgSO$_4$. 01% gelatin) and incubated at 4° C. overnight. The SM buffer was removed and each plate was washed with 1 ml of SM buffer. The collected SM buffer was aliquoted in 1.5 ml eppendorf tubes containing 25 μl of chloroform and stored at 4° C. (Sambrook, J. et al., Molecular cloning. A laboratory Manual 2nd. ed. Vol. 1, 2 and 3. Cold Spring Harbor Laboratory Press, NY (1989)). The amplified phage was titered as previously described, and DMSO was added to a final concentration of 7% and the library was stored at −80° C.

Preparation of Rabbit anti-Acetyl CoA Synthetase

Acetyl CoA synthetase was purified from a bovine mammary gland taken 60 days post-partum as previously described (Qureshi, S. and R. M. Cook, J Agric. Food Chem. 23:555 (1975); Ricks, C. A. and R. M. Cook, J. Dairy Sci. 64:2324 (1981)). The procedure involved (NH$_4$)$_2$SO$_4$ fractionation of a mitochondrial extract followed by column chromatography using DEAE-cellulose and calcium phosphate gel. Fifty μg of acetyl CoA synthetase in 300 μl of potassium phosphate buffer, pH 7.0, and 300 μl of Freund's complete adjuvant (Sigma Chemical Co. F5881) were injected into New Zealand White rabbits. Second and third injections were at 2 week intervals using half the amount in the first injection and 150 μl of Freund's incomplete adjuvant (Sigma Chemical Co. F5506). Blood serum was collected two and four weeks after the third injection. IgG was purified using DEAE Affi-Gel Blue Gel (Bio-Rad 153–7307).

Screening of Mammary Gland λgt11 Library With Rabbit Anti-Holstein ACS IgG

This procedure was adapted from Mierendorf et al (Mierendorf, R. C., et al., Methods Enzumol. 152:458 (1987)). The λgt11 library was screened with rabbit anti-Holstein mammary gland ACS and goat anti-rabbit gamma globulin containing alkaline phosphatase.

One ml of an overnight culture of $E.$ $coli$ (Y1090rK$^-$) was added to 50 ml of LB media, pH 7.5, (10 g bacto-tryptone, 5 g bacto-yeast, 5 g NaCl, 10 mM MgCl$_2$, 50 μg/ml of ampicillin and 0.2% maltose, in one liter of sterile water), and incubated aerobically at 37° C. until the O.D. at 600 nm was 0.5. This requires about 3 hours. Then 0.6 ml (10$^8$ cells) were incubated with 10$^5$ λgt11 for 20 minutes at room temperature. Infected $E.$ $coli$ Y1090rK$^-$ were mixed with 7.5 ml of top agarose, poured on a 150 mm agar plate, and incubated at 42° C. for 4 hours. The plate was overlaid with a dry nitrocellulose filter which previously had been saturated with 10 mM IPTG in sterile deionized water. The plates were then incubated at 37° C. for 8 hours. The nitrocellulose filter was washed with a Tris-buffered saline plus Tween 20 (TBST) (10 mM Tris-HCl, pH 8.0, 150 mM NaCl, and 0.05% Tween 20) and then blocked with 1% BSA in TBST. The filter was incubated with 7.5 ml of rabbit anti-Holstein ACS for 30 minutes and then washed 3 times with 20 ml aliquots of TBST. Each wash was for 5 minutes at room temperature. The filter was then incubated at room temperature for 30 minutes with 15 ml of TBST containing a 1:7,500 dilution of goat anti-rabbit gamma globulin-alkaline phosphatase conjugate. The filter was washed three times with 20 ml aliquots of TBST. To identify plaques with ACS fusion protein, the filter was incubated with 10 ml of solution containing 100 mM Tris-HCl, pH 9.5, 100 mM NaCl, and 5 mM Mg Cl$_2$, 66 μl of nitro blue tetrazalium (50 mg/ml in 70% dimethyl formamide), and 33 μl of 5-bromo-4-chloro-3 indolyl phosphate (50 mg/ml in dimethyl formamide) and incubated in the dark at room temperature for 35 minutes. Positive plaques appear as purple dots on the nitrocellulose filter. Approximately 750,000 plaques were screened.

ACS Enzyme Assay

Acetyl coenzyme A synthetase was assayed using the acetate dependent disappearance of the sulfhydryl group of coenzyme A as described by Qureshi et al. (Qureshi, S. and R. M. Cook, J. Agric. Food Chem. 23:555 (1975)). In a total volume of 0.2 ml the reaction mixture contained 5 μmol of MgCl$_2$, 0.17 μmol of coenzyme A, 1.1 μmoles of ATP, 5 μmoles of K acetate, 16 μmol of Tris-HCl, pH 8.6, and 5 to 10 μg of enzyme protein. Blank tubes did not contain coenzyme A and standard tubes did not contain acetate. The enzyme assay was carried out at 37° C. for 10 minutes. The reaction was stopped by adding 2.8 ml of a 5:1:1 mixture of the following solutions: sodium nitroprusside 6.75 g/250 ml water, sodium carbonate-sodium syanide 106 g and 2.2 g, respectively, in 500 ml water and saturated sodium chloride (Grunert, R. R. and P. H. Phillips, Arch. Biochem. 30:217 (1951)) and the optical density at 520 nm recorded exactly after 30 seconds. The enzyme protein was adjusted to an optical density difference between standard and complete reaction tubes of 0.075 to 0.250. An optical density difference of 0.185 is equivalent to the disappearance of 0.1 μmol of coenzyme A. One unit of enzyme activity is defined as the activation of 1 μmol of acetate per hour. Specific enzyme activity is expressed as units/mg of protein.

ACS activity of fusion proteins AR8 and ATC5 was determined in protein isolated from *E. coli* Y1089r$^{K-}$ grown in the presence of λgt11 carrying AR8 or ATC5 cDNA. Briefly, *E. coli* Y1089rK$^-$ was grown in LB medium at 37° C. to late log phase. Then, *E. coli* Y1089r$^{K-}$ was infected with λgt11 at a multiplicity of infection (MOI) of 5 for 20 minutes at 32° C., added to top agar and plated as previously described. Colonies were isolated and tested at 32 and 42° C. to determine lysogens. Then, 100 μl of liquid broth media were inoculated with a single colony and incubated at 32° C. to OD of 0.5 at 600 nm, followed by incubation at 42° C. for 20 minutes. The culture was further incubated aerobically at 37° C. for 4 hours in the presence of 10 mM IPTG. The culture was centrifuged at 3,000×g for 5 minutes at 24° C. and resuspended in TEP buffer (100 mM Tris-HCl, pH 7.4, 10 mM EDTA, 1 mM phenylmethylsulfonyl fluoride) and stored at −70° C. The cells were lysed by freezing and thawing 4 times followed by sonication for 10 minutes in a waterbath sonicator (Branson Ultrasonic Corporation Cat. # 26373). The extract was centrifuged at 11,000×g for 10 minutes and the supernatant taken for enzyme assay.

Isolation of λgt11 AR8 and AT5 DNAs by Using PEG 8000

Ten ml of LB medium were inoculated with *E. coli* Y1090rK$^-$ and incubated at 37° C. overnight under aerobic conditions. Prewarmed LB medium (50 ml) was inoculated with 1 ml of the overnight culture and incubated at 37° C. under aerobic conditions to OD of 0.5 at 600 nm (3–4 hours). Five ml of the bacteria were inoculated with 10$^{10}$ pfu of λgT11, incubated at 37° C. for 20 minutes, then added to 500 ml of prewarmed LB medium. The flask was incubated at 37° C. under aerobic conditions until lysis occurred (4–6 hours). Ten ml of chloroform were added and the flask was incubated at 37° C. under aerobic conditions for 15 minutes. The culture was cooled to room temperature and five hundred μg of pancreatic DNase I and 500 μg of RNase were added to 500 ml of lysed culture and incubated 30 minutes at room temperature. Solid NaCl was added to a final concentration of 1 M. The flask was placed on ice for 1 hour and the contents centrifuged at 11,000×g for 10 minutes at 4° C. To isolate λgt11, solid polyethylene glycol 8,000 (PEG) was added to the supernatant at room temperature to a final concentration of 10% (w/v) and the material was stored overnight at 4° C. PEG was collected by centrifuging at 11,000×g for 10 minutes at 4° C. (Yamamoto, K. R., et al., Virology 40:734 (1970)). The PEG pellet was suspended in 5 ml of TM buffer (50 mM Tris-HCl, pH 7.8, and 10 mM Mg SO$_4$) and λgt11 was removed from the PEG by extracting with an equal volume of chloroform. Fifty μl of chloroform were added to the aqueous phase which contains λgt11 and the material was stored at 4° C. Titers were determined as previously described.

Purifying λgt11 DNA Using Ultracentrifugation in a Glycerol Gradient

λgt11 was purified by centrifuging in a glycerol gradient. Eight ml of 5% glycerol in TM buffer were layered over 6 ml of 40% glycerol in TM buffer. Thirteen ml of λgt11 in TM buffer were layered over the 5% glycerol and the contents were centrifuged at 141,000×g for 2.5 hours at 4° C. The supernatant was discarded and the λgt11 pellet was suspended in 0.5 ml of TM buffer and transferred to a microcentrifuge tube. To remove any *E. coli* DNA and RNA, pancreatic DNase and RNase were added to a final concentration of 5 μg/ml and 1 μg/ml, respectively. The reaction mixture was incubated at 37° C. for 30 minutes. EDTA, pH 8.0, was added to a final concentration of 20 mM. The reaction mixture was then digested 1 hour at 56° C. with proteinase K at a concentration of 0.5 μg/ml in the presence of 0.5% SDS. After digestion, the reaction mixture was cooled to room temperature and extracted once with phenol saturated with TE buffer, once with a 1:1 mixture of chloroform and phenol saturated with TE buffer, and finally once with chloroform. The aqueous phase was dialyzed overnight at 4° C. against 3 liters of TE buffer, pH 8.0 (Vande Woude, G. F. et al., Proc. Natl. Acad. Sci. 76:4464 (1979)). The λgt11 DNA was then ethanol precipitated as previously described.

DNA Restriction Digest

The reaction mixture used to isolate cDNA from λgt11DNA contained 1 μl of λgt11 (0.28 μg), 1 μl of a buffer containing 10 mM Tris-HCl, pH 7.0, 200 mM NaCl, 1 mM EDTA, 0.5 mM DTT, 0.2% (v/v) Triton X-100, and 50% (v/v) glycerol, 1 μl of EcoRI (8–12 units), and 7 μl of sterile deionized water. The reaction was carried out at 37° C. for 1 hour. Then 2 μl of gel loading buffer were added that contained 0.25% bromophenol blue, 0.25% xylene cyanol FF, and 15% ficoll 400 in sterile deionized water. The reaction mixture was heated 5 minutes at 65° C. and the entire mixture subjected to agarose gel electrophoresis. This procedure was used for all restriction enzyme digests except that a buffer appropriate for the particular restriction enzyme was used.

DNA Electrophoresis

For electrophoresis of DNA, a 0.8% agarose solution was prepared in TBE buffer (0.089 M Tris-base, 0.089 M boric acid, 0.002 M EDTA, pH 8.0) by heating in a microwave oven. The solution was cooled to 50° C. and ethidium bromide added to a final concentration of 0.5 μg/ml. Seventy ml of the solution were poured into a 11×9.5 cm plate using a 10-well comb to sample wells 0.7 cm wide. After the solution gelled, the comb was removed and TBE electrophoresis buffer was added to the apparatus to a height of about 0.25 ml above the gel. DNA samples were placed in the sample wells and a potential difference of 50 V applied until the tracking dye moved about two thirds of the length of the gel (Sambrook, J., et al., Molecular cloning. A laboratory manual. 2nd ed. Vol. 1, 2 and 3. Cold Spring Harbor Laboratory Press, NY (1989)). The gel was examined under UV light. Gels were photographed with a polaroid camera.

DNA Elution

The section of agarose gel containing the DNA to be examined was placed in the slot of an electro-eluter (IBI UEA Cat. # 46000). TBE buffer was added and air bubbles were removed from the DNA collection channels. Seventy μl of solution containing 10 mM Na acetate and 0.025% bromophenol blue were placed in the DNA collecting channel. A potential difference of 100 V was applied for 30 minutes. The electro-eluted DNA was transferred to a microcentrifuge tube and precipitated with absolute ethanol for 10 minutes at room temperature, washed with 300 μl of 70% ethanol, dried in a speedvac, and dissolved in minimal volume of TE buffer pH 7.6.

Subcloning cDNA into pUC19

One μg of pUC19 was digested with 10 units (1 μl) of EcoRI in a total volume of 10 μl for one hour at 37° C. Then 1 μl (one unit) of calf intestinal alkaline phosphatase and 2 μl of dephosphorylation buffer (500 mM Tris-HCl, pH 8.5, 1 mM EDTA) were added and the total volume adjusted to 20 μl with sterile deionized water. The reaction mixture was incubated 15 minutes at 37° C. and then extracted once with a 1:1 mixture of chloroform and phenol equilibrated with TE buffer and once with chloroform. DNA in the aqueous phase was ethanol precipitated as previously described, washed once with 70% ethanol, dried 1 minute using a speedvac, and dissolved in 10 μl of TE buffer, pH 7.6. Two μl (200 ng) of this pUC19 were examined using 0.8% agarose gel to confirm that pUC19 was digested with EcoRI. Then 200 ng were added to 100 ng of cDNA with EcoRI ends, the volume adjusted to 8 μl, and the contents incubated 5 minutes at 45° C. One μl of 10×T$_4$ DNA ligase buffer and 1 Weiss unit (1 μl) of T$_4$ DNA ligase were added and the tube incubated 4 hours at 16° C. The DNA was then precipitated with ethanol as previously described, washed, dried in a speedvac, and dissolved in 5 μl of sterile deionized water.

Transformation of E. coli DH5α with pUC19

Subcloning efficiency E. coli DH5α competent cells (BRL cat. # 8265SA) were used for routine subcloning into plasmid vectors according to the manufacturer's procedure. E. coli DH5α stored at −70° C. was thawed on ice. Five μl of pUC19 containing cDNA were added to 50 μl of E. coli DH5α, mixed gently with the pipet tip, and incubated 30 minutes on ice. The cells were heat shocked by incubating 20 seconds at 37° C. followed by incubation 2 minutes on ice. Then 950 μl of LB medium were added and the tube incubated 1 hour at 37° C. The cells were isolated by centrifuging 20 seconds at 3,000×g. Eight hundred μl of supernatant were removed and the cells were suspended in the remaining 200 μl of LB medium. To isolate cells containing recombinant pUC19, 40, 60, and 100 μl of the cell suspension were spread on agar plates containing IPTG, X-Gal, and ampicillin using a sterile glass rod and incubated overnight at 37° C. Positive colonies were selected and cultured in 5 ml of LB medium containing ampicillin (50 μg/ml), and then incubated aerobically overnight at 37° C. The DNA mini prep described above was used to amplify and further purify AR8 and ATC5. The plasmid was digested with EcoRI and the cDNA examined using 0.8% agarose to confirm the presence of cDNA.

Small Scale Plasmid DNA Preparation

This protocol is a modification of the methods of Birnboim and Doly (Birnboim, H. C., et al., Nucleic Acids Res. 7:444 (1979)) and Ish-Horowicz and Burke (Ish-Horowicz, D., et al., Rapid and efficient cosmid cloning. Nucleic Acids (1981)). Fifteen ml of LB media containing 50 μg/ml ampicillin were inoculated with E. coli DH5-α infected with recombinant plasmid (pUC19) and grown overnight at 37° C. in an orbital rocker. Then 1.5 ml were centrifuged at 12,000×g for 2 minutes in a microcentrifuge. The supernatant was discarded and an additional 1.5 ml of culture added followed by centrifuging 2 minutes. The cells were suspended in 100 ml of a solution containing 50 mM glucose, 10 mM EDTA, and 25 mM Tris-HCl, pH 8.0. After standing 5 minutes at room temperature, 200 μl of a freshly prepared solution containing 0.2 M NaOH and 1% sodium dodecyl sulfate (SDS) were added and the tube placed in ice for 5 minutes. Then 150 μl of ice cold 3 M potassium acetate, pH 4.8, were added and the contents mixed by briefly vortexing and then incubated on ice for 5 minutes. The contents were centrifuged at 12,000×g for 5 minutes and the supernatant transferred to a clean microcentrifuge tube and centrifuged at 12,000×g for 5 minutes. The supernatant was transferred to a clean tube and RNase was added to a final concentration of 50 μg/ml. The tube was incubated 30 minutes at 37° C. The sample was extracted two times with a 1:1 mixture of chloroform and phenol equilibrated with TE buffer and once with chloroform. DNA was precipitated by adding 0.1 volume of 3 M sodium acetate, pH 5.2, and 1 ml of ice cold ethanol kept at −20° C., and left at −20° C. overnight. The tube was then centrifuged at 12,000×g for 10 minutes. The pellet was washed twice with 70% ethanol and dried for 5–10 minutes in a speedvac. DNA was dissolved in 16.8 μl of water, then 3.2 μl of 5 M NaCl were added. To further purify the DNA, 20 μl of a 13% aqueous solution of PEG 8,000 were added, mixed gently, and the contents incubated on ice in a cold room for 1 hour. The sample was centrifuged at 12,000×g for 10 minutes at 40° C. The DNA pellet was washed once with 1 ml of ice cold 70% ethanol, dried in a speedvac, and then dissolved in 20 μl of water. This DNA sample was sequenced using Sequenase (Version 2.0, U.S. Biochemicals).

Random primer labeling of DNA fragments

DNA fragments were routinely labeled to high specific activity by the random hexamer priming method (Feinberg, A. P. and B. Vogelstein, Anal. Biochem. 132:6 (1983)). A kit based on this method was obtained from Boehringer Mannheim labeling (kit # 1004760) and used as described by the manufacturers. 50 ng of DNA in 9 μl of sterile deionized water were heated at 95° C. for 10 minutes and cooled in ice. The complete reaction mixture contained 50 ng DNA in 9 μl, 2 μl of random primer buffer (2 mM Tris-HCl pH 7.0, 0.2 mM EDTA, 4 mg/ml BSA, 2 M N-(2-hydroxyethyl) piperazine-N'-(2-ethanesulfonic acid) (HEPES) pH 6.6 and random hexanucleotide primers), 3 μl of a mixture of dATP, dGTP, and dTTP each at 0.5 mM, 5 μl of 3.3 mM [α$^{32}$P] dCTP containing 50 μCi (3,000 Ci/mmol), and 1 μl (2 units) of Klenow enzyme (exonuclease free). The reaction was carried out at 37° C. for 1 hour and stopped by adding 2 μl of 200 mM EDTA. Free [α$^{32}$P]dCTP was removed from the reaction mixture using Sephadex G-50 spun-column chromatography.

Spun-Column Chromatography

Sterile glass wool was placed in the bottom of a 1 ml plastic syringe and the syringe filled with either Sephadex G-50 (for removing [α$^{32}$P]dCTP in DNA labeling reactions) or Sephacryl S-400 (for size fractionation of cDNA) in TE buffer pH 8.0. The syringe was placed in a 15 ml plastic centrifuge tube and centrifuged at 1,600×g for 3 minutes using a swinging bucket rotor. This process was repeated until the volume of the packed column was 0.9 ml. The column was equilibrated 3 times with the addition of 0.1 ml aliquots of TE buffer pH 8.0. DNA in 0.1 ml was placed on the column and collected in a microcentrifuge tube by centrifuging at 1,600×g for 3 minutes (Sambrook, J., et al., Molecular cloning. A laboratory manual. 2nd. ed. vol. 1, 2 and 3. Cold Spring Harbor Laboratory Press, NY (1989)).

Screening cDNA Library with $^{32}$P-Labeled DNA Probes

Oligonucleotide screening was performed as described by Grunstein and Hogness (Grunstein, M. and D. S. Hogness, Proc. Natl. Acad. Sci. 72:3961 (1975)) Agar plates containing E. coli Y1090rk$^-$ infected with λgt11 were incubated overnight at 37° C. then at 4° C. for 2 hours before dry nitrocellulose filters were placed on the agar. After 30 to 60 seconds, the filters were removed using blunt ended forceps. The filters were then placed colony side up on 3 mm Whatman chromatography paper previously saturated with 10% aqueous SDS. After 3 minutes, the filter was placed on 3 mm paper saturated with denaturing solution (0.5 M NaOH and 1.5 M NaCl in $H_2O$). After 5 minutes the nitrocellulose filter was transferred to 3 mm paper saturated with neutralizing solution (1.5 M NaCl and 0.5 M Tris-HCl pH 7.4). After 5 minutes the filter was transferred to a final 3 mm paper saturated with 2×SSC (1×SSC is 150 mM NaCl, 15 mM Na citrate pH 7.0). After 5 minutes the nitrocellulose filter was removed from the 3 mm paper, dried at room temperature, and baked in a vacuum oven for two hours at 80° C. (Benton, W. C. and R. W. Davis, Science. 196:180 (1979). The filter was then placed in 2×SSC for 5 minutes followed by washing in a prewashing solution containing 5×SSC, 0.5×SDS, and 1 mM EDTA. To reduce background, bacterial debris was gently removed from the surface of the nitrocellulose filter using lintless tissue premoisturized with prewashing solution.

Each filter was incubated in 15–20 ml prehybridization solution [28.4 ml $H_2O$, 50 ml formamide, 16.6 ml 6×SSC, 5 ml of 1×Blotto (5% non-fat dried milk dissolved in water containing 0.02% sodium azide) and poly($A^+$) mRNA to a concentration of 1 μg/ml] for at least 4 hours at 42° C. The $^{32}$P-labeled double stranded DNA was denatured by heating for 5 minutes at 100° C. and then placed on ice. The denatured probe was added to the prehybridization solution containing the filter and incubated overnight at 42° C. The filter was then washed two times with 2×SSC and 0.1% SDS for 15 minutes at room temperature, then one time with a solution of 0.1% SDS in 0.1×SSC for 30 minutes at 68° C. The filters were dried at room temperature, wrapped in Saran Wrap, and exposed to Kodak XR film for 24 to 48 hours at −70° C. with an intensifying screen (Sambrook, J., et al., Molecular cloning A laboratory manual. 2nd. ed. Vol. 1, 2 and 3. Cold Spring Harbor Laboratory Press, NY (1989)). Plaques which gave positive signals on the filters were isolated and rescreened until plaque purified.

Isolation of Genomic DNA

Two g of mammary gland tissue were taken from a Holstein cow 60 days post-partum, minced, and placed in 0.7 ml of lysis buffer (0.05 m Tris-HCl, pH 8.0, 0.1 M EDTA, 0.5% SDS, and 350 μg of proteinase K) and incubated 14 hours at 55° C. with gentle mixing. Then 0.7 ml of phenol saturated with TE were added and the tube gently mixed for 3 minutes and centrifuged at 12,000×g for 3 minutes at room temperature. The aqueous phase was extracted with 0.7 ml of a 1:1 mixture of chloroform and phenol saturated with TE buffer, pH 8, by mixing gently for 2 minutes and then centrifuged for 3 minutes. The aqueous phase was transferred to a 1.5 ml centrifuge tube and DNA was precipitated by adding 70 μl of Na acetate (pH 6.0) and 1.4 ml of 100% ethanol. After standing at room temperature for 5 minutes, the tube was centrifuged for 30 seconds at room temperature and the DNA precipitate suspended in 1 ml of 70% ethanol and centrifuged again for 1 minute. The DNA was dried in a speedvac for 2 minutes and then dissolved in 0.1 ml of TE buffer, pH 7.6, by incubating at room temperature overnight and then stored at 4° C. (Blin, N. and D. W. Stafford, Nucleic Acids Res. 3:2303 (1976)).

Southern Blots

DNA was subjected to agarose gel electrophoresis as previously described. The gel was then gently agitated for 30 minutes in 0.4 M NaOH. A Zeta-Probe membrane (Bio-Rad) having the same dimensions as the gel was placed in 0.4 M NaOH for 15 minutes. An empty pipette tip box was placed in a plastic container containing transfer solution (0.4 m NaOH) then a plexiglass plate was placed on top of the box. A piece of Whatman 3 mm paper was placed on the plexiglass plate such that the side of the paper extended into the transfer solution. The 3 mm paper was equilibrated with transfer solution. The agarose gel was then inverted and placed on the 3 mm paper. Air bubbles were removed using gentle pressure. Next the Zeta-Probe membrane was placed on top of the gel and air bubbles removed. The membrane was covered with 2 layers of 3 mm filter paper previously equilibrated with 0.4 m NaOH. Air bubbles were removed by gently rolling a pasture pipette over the 3 mm filter paper. A stack of paper towels was cut just smaller than the 3 mm paper and placed on the 3 mm paper. The area of the gel was held in place on top of the filter paper with glass plates. Transfer of DNA was allowed to precede overnight (Southern, E. M., J. Mol. Biol. 98:503 (1975)). The Zeta-Probe membrane was washed once with a solution containing 0.2 M Tris-HCl, pH 7.5, and 2×SCC for 15 minutes with gentle shaking. The membrane was blotted dry with Whatman No. 1 filter paper, sandwiched between 3 mm paper, and heated in a vacuum oven for 1 hour at 80° C.

Northern Blots

RNA was subjected to electrophoresis in agarose formaldehyde gel as previously described. The gel was washed two times for 15 minutes each at room temperature in DEPC treated water and then placed in a solution containing 50 mM NaOH and 10 mM NaCl for 15 minutes at room temperature. The gel was then placed in 20×SSC for 15 minutes. The buffer used to transfer RNA to a Hibond membrane (Amersham # RPN.303N.) previously equilibrated with DEPC water was 20×SSC. The apparatus and procedure to transfer RNA was as described for southern blots except that the two layers of 3 mm paper placed on the membrane were equilibrated with 20×SCC (Fourney, R. M., et al., Northern blotting: Efficient RNA staining and transfer. Bethesda Res. Lab. Focus. 10(1):5 (1988); Wreschner, D. H. and M. Herzberg, Nucleic Acids Res. 12:1349 (1984)). After drying, RNA was fixed to the membrane by exposing to UV light for 10 seconds and then baked in a vacuum oven at 80° C. for 2 hours.

Sequencing Gel

The glass plates (38×40.5 cm and 38×44.5 cm) with spacers were held together by paper clamps. The 8% sequencing gel contained 20 ml of 20% acrylamide (96.5 g acrylamide, 3.35 g methylene-bis-acrylamide, 233.5 g ultrapure urea, 100 ml 5×TBE, sterile deionized $H_2O$ to 500 ml), 30 ml of urea mix (233.5 g urea, 100 ml 5×TBE, sterile deionized $H_2O$ to 500 ml), 0.4 ml of 10% ammonium persulfate, and 20 μl N-N-N'-N'-tetramethylethylenediamine (TEMED). The solution was poured using a 50-ml syringe. A 65 well sequencing comb was inserted and the gel solution was allowed to polymerize at room temperature. After polymerization the gel was mounted in a vertical electrophoresis apparatus (International Biotechnologies Inc. Cat.# 80000) and the comb was removed. Electrophoresis buffer (TBE, pH 8.3) was added to the top and bottom reservoir. Air bubbles at the bottom of the gel were removed using a bent hypodermic needle attached to a syringe (Sambrook, J. et al., Molecular cloning. A laboratory manual. 2nd. ed. Vol. 1, 2 and 3. Cold Spring Harbor Laboratory Press. NY (1989)). The samples were loaded and electric power applied (55 W).

DNA Sequencing

DNA was sequenced in both directions using Sequanase kit (Version 2.0, U.S. Biochemicals) which implies the chain termination method (Sanger, F., et al., Proc. Natl. Acad. Sci. 74:5463 (1977)). DNA in 20 μl was denatured by adding 15.2 μl of a solution containing 2 M NaOH and 2 mM Tris-HCl, and incubating 5 minutes at room temperature. Then the tube was placed in ice and 8 μl of 1 M Tris-HCl, pH 4.5, and 3 μl of 3 M Na acetate were added followed by 75 μl of ice cold 100% ethanol. The sample was stored 20 minutes at −70° C. and then centrifuged at 12,000×g for 5 minutes. The DNA precipitate was washed with 200 μl of ice cold 70% ethanol, centrifuged, and the DNA dried at room temperature using a speedvac. The DNA was dissolved in 7 μl of sterile deionized water. The 5 μg of denatured DNA in 7 μl was annealed to 1 μl of pUC19 forward primer (5'-GTTTTCCCAGTCACGAC-3') (SEQ ID NO:7) in the presence of 2 μl of sequencing buffer (200 mM Tris-HCl, pH 7.5, 100 mM $MgCl_2$, 250 mM NaCl). A second tube was prepared using 1 μl of pUC19 reverse primer (5'-CAGGAAACAGCTATGAC-3') (SEQ ID NO:8). The reaction mixtures were incubated 30 minutes at 37° C. The following was added to the annealed DNA: 1 μl of 1 M DTT, 2.0 μl of solution containing 1.5 μM each of dGTP, dCTP, and dTTP, 0.5 μl (4 μCi) of [$^{35}$S]dATP, and 2 μl (3 units) of Sequanase. This labeling reaction tube was incubated 5 minutes at room temperature. For the termination reaction, 2.5 μl of ddGTP solution (dGTP, dATP, dCTP, and dTTP each at 80 μM; 8 μM ddGTP, 50 mM NaCl) were placed in a 1.5 ml microcentrifuge tube labeled G. Similarly, tubes labeled A, T, and C contained 2.5 μl of the ddATP, ddTTP, and ddCTP termination solutions. To each of these 4 tubes prewarmed to 37° C., 3.5 μl of labeling reaction were added. The tubes were briefly centrifuged and incubated at 37° C. for exactly 5 minutes. The reaction was terminated by adding 4 μl of stop buffer containing 95% formamide, 20 mM EDTA, 0.05% bromophenol blue, 0.05% xylene cyanol FF, thoroughly mixed, and then stored on ice before loading on the sequencing gel. Before loading, the sample was heated 2 minutes at 70° C. and then placed on ice. 2.5 μl were loaded on the sequencing gel.

Purification of Rabbit anti-ACS IgG

Nitrocellulose filters containing immobilized proteins were prepared as described previously for immunological screening (*E. coli* Y1090r$^{k-}$ was infected with λgt11 containing ATCS). After blocking the filters with 1% BSA, they were dried and treated 1 hour with a 1:200 dilution of rabbit anti-mammary gland ACS in TBST buffer and then washed 3 times with 7.5 ml of TBST. The IgG bound to ATC5 fusion protein was eluted from the nitrocellulose filter with 3 one minute washes of 7.5 ml of a solution containing 5 mM glycine-HCl, pH 2.3, 150 mM HCl, 0.5% Triton X-100, and BSA (100 μg/ml). The combined washes were made 50 mM with Tris-HCl, pH 7.4 (Weinberger, C. et al., Science, 228:740 (1985)). This IgG preparation was used in heart-ACS assays and to detect ACS in Western blots of protein from mammary gland, heart, kidney, liver, and spleen.

Immunoprecipitation of Heart ACS Activity

Heart ACS was the $(NH_4)_2SO_4$ precipitate of the mitochondrial extract of fresh tissue (Qureshi, S. and R. M. Cook, J. Agric. Food Chem. 23:555 (1975)). The first antibody was rabbit anti-ACS affinity purified. The second antibody was goat anti-rabbit IgG (Sigma). Ten μg of protein in 50 μl of 0.4 M Tris, pH 8.6, were incubated with 250 μl of affinity purified rabbit or with 250 μl buffer (control) for one hour. 50 μl of the second antibody containing 20 μg of IgG were added to the tube containing antibody and 50 μl of buffer were added to the control and the tubes incubated for another hour. In a third tube, 10 μg of protein in 50 μl of Tris 0.4 M, pH 8.6, were incubated with 250 μl of buffer for one hour and then with 50 μl of the second antibody containing 20 μg of IgG for another hour (Weinberger, C., et al., Science. 228:740 (1985)). The tubes were centrifuged at 12,000×g for 30 minutes, and the supernatant assayed for enzyme activity as above.

SDS-Polyacrylamide Gel Electrophoresis

Proteins were resolved in 8% polyacrylamide. A stock solution of 30% acrylamide/bis was prepared by dissolving 29 g of acrylamide, 1 g of N-N'-methylene-bis-acrylamide in 60 ml of sterile deionized water, heating 10 minutes at 37° C., diluting to a final volume of 100 ml, and filtering through a Nalgene filter having a pore size of 0.45 microns. The 8% polyacrylamide gel mixture consisted of 12.8 ml of 30% acrylamide/bis, 12 ml of 1.5 M Tris-base, pH 8.8, 22.5 ml sterile deionized water, 0.48 ml of 10% SDS (Laemmli, 197), which was mixed and degassed for 10 minutes, and then 0.36 ml of ammonium persulfate and 25 μl of TEMED added. The solution was poured between two glass plates 16×19.5 and 20×19.5 cm in dimensions leaving a 4 cm space at the top. The gel was overlayed with 0.5 ml of water-saturated isobutanol. After 45 minutes at room temperature, the isobutanol was removed and the top of the gel was washed with sterile deionized water. The stacking gel (4% acrylamide) was prepared by mixing 2 ml of 30% polyacrylamide/bis, 3.75 ml of 0.5 M Tris-base, pH 6.8, 9 ml of sterile deionized water, and 0.15 ml of 10% SDS. The solution was degassed for 10 minutes then 75 μl of 10% ammonium persulfate and 8.5 μl of TEMED added. After pouring this solution on top of the resolving gel, a 15 well comb (0.6 cm wide, 2.8 cm long, and 0.1 cm thick) was inserted in the stacking gel solution (Davis, B. J., Ann. N. Y. Acad. Sci. 121:404 (1964)). The gel was kept in a vertical position for 90 minutes then the comb was removed, the gel was mounted in a vertical electrophoresis apparatus, and electrophoresis buffer (25 mM Tris-base, 25.0 mM glycine, pH 8.3, 0.1% SDS) added to the top and bottom reservoirs. Air bubbles were removed from the bottom of the gel using a bent 20 gauge needle and syringe. The protein samples and molecular weight marker were heated in the loading buffer (50 mM Tris-HCl, pH 6.8, 100 mM DTT, 2% SDS, 0.1% bromophenol blue, and 10% glycerol) at 100° C. for 3 minutes. Then the samples were placed in the wells and 13 mA of current were applied overnight.

Western Blot

The plates from the SDS polyacrylamide gel electrophoresis of proteins were separated using a spatula and the orientation of the gel marked. A nitrocellulose membrane (Schlucher and Schuell Cat. # 68380) was equilibrated with transfer buffer (1.5 mM Tris-base, pH 8.3, 120 mM glycine, and 20% methanol). The gel was placed in transfer buffer and the stacking gel removed. Four sheets of 3 mm paper were equilibrated with transfer buffer. One-half of the cassette of a Hoeffer electro transferring apparatus (Hoeffer Scientific Instrument Cat. # SE600) was placed in a tray containing transfer buffer. The sponge supplied with the apparatus was placed on top of the cassette. Then the following was placed on the sponge: 2 sheets of Whatman 3 mm paper, 1 nitrocellulose membrane, the polyacrylamide gel, the remaining 2 sheets of 3 mm paper, and a second sponge. The second half of the cassette was assembled to complete the sandwich. The cassette was removed from the tray and placed in the Hoeffer transfer tank. The tank containing transfer buffer and cassette was cooled using circulating ice water. One hundred V were applied for 2 hours in a cold room (Towbin, H. et al., Proc. Natl. Acad. Sci. 76:4350 (1979); Burnette, W. N. Anal. Biochem. 112:195 (1988)). Then the gel was stained with Coomassie blue to determine if protein transfer was complete. The nitrocellulose filter was then examined using rabbit anti-Holstein mammary gland ACS and Promega immunological screening kit as previously described.

Slot Blot

300 µl of a mixture of 500 µl formamide, 162 µl of formaldehyde (37% solution) and 100 µl of 10×MOPS buffer were added to 100 µl of the RNA sample (1–10 µg) and incubated at 65° C. for 5 minutes. The sample was then chilled on ice and 100 µl of cold 20×SSC were added. Three layers of Bio-Dot SF filter paper (Bio-Rad Cat. # 162-0161) were equilibrated in 10×SSC and placed on the filter support plate of the slot-blot apparatus (Bio-Rad Cat. # 170-6542). A nylon membrane (Hybond-N, Amersham RPN.303N) was also equilibrated with 10×SSC and placed over the 3 layers of filter paper. The sample well plate was clamped into place and a low vacuum applied. When the buffer had drained from the wells the vacuum was disconnected and the RNA samples were loaded in the wells. Low vacuum was applied again until the solution drained from the wells. Vacuum was disconnected and 500 µl of 10×SSC were loaded in the wells. Vacuum was applied until the buffer drained. This last procedure was repeated. RNA was fixed to the membrane by exposure to UV light for 30 seconds, dried 30 minutes at room temperature, then under vacuum for 2 hours at 80° C. Prehybridization was 1 hour and hybridization to $^{32}$P-labeled probe was overnight at 42° C. in 5×SSC, 5×Denhardt's solution (1×Denhardt's solution is 0.02% BSA, 0.02% ficoll, and 0.02% polyvinyl-pyrrolidone), 0.5% SDS, and 10 µg/ml denatured herring sperm DNA (Boehringer Mannheim 223 646). After hybridization the membrane was washed two times for 10 minutes each at room temperature with 2×SSC and 0.1% SDS and then 30 minutes at 42° C. with 0.5×SSC and 0.1% SDS (Thomas, P. S., Proc. Natl. Acad. Sci. 77:5201 (1980); White, B. A. and F. C. Bancroft, J. Biol. Chem. 257:8569 (1982)). Autoradiography was for 48–72 hours at −80° C. A densitometer (Bio-Rad 165-2040) was used to examine the radiogram. A standard curve was prepared using ATC5 cDNA at concentrations of 1.6–200 pg.

Large Scale Preparation of Plasmid DNA

E. coli DH5α transformed with pUC19-ATC5 or pUC19-AR8 was grown in 500 ml LB medium in a shaker overnight. The bacterial cells were harvested by centrifugation at 6,000×g at 4° C. for 10 minutes. The pellet was washed in 100 ml STE buffer (0.1 M NaCl, 10 mM Tris-HCl, pH 8.0, 1 mM EDTA) and the bacterial cells were collected by centrifugation at 6,000×g for 10 minutes at 4° C. The pellet was resuspended in 10 ml GET buffer (50 mM glucose, 25 mM Tris-HCl pH 8.0, 10 mM EDTA) then 10 ml of freshly prepared solution of 0.2 N NaOH and 1% SDS were added with thorough mixing. The tube was stored at room temperature for 10 minutes then 20 ml of ice cold 3 M potassium acetate, pH 4.8, were added and the contents mixed by inverting the tube several times. Then the tube was stored on ice for 10 minutes. The bacterial lysate was centrifuged at 15,000×g for 20 minutes at 4° C. The supernatant was transferred to a sterile Corex tube and 6 ml of isopropanol were added, mixed and incubated at room temperature for 15 minutes. The tube was centrifuged at 12,000×g for 20 minutes at room temperature. The pellet was washed with 5 ml of 70% ethanol and dried in a speedvac for 5 minutes. The dry pellet was dissolved in 11.3 ml of sterile TE buffer, pH 7.5. Then 11.55 g of CsCl were added to the tube and dissolved by inverting the tube several times, and 300 µl of ethidium bromide (10 mg/ml) were added. The solution was placed into a Beckman Ti 65 Quick-Seal tube and the tube sealed and centrifuged at 55,000×g overnight at 20° C. The supercoiled DNA was collected by inserting an 18-gauge hypodermic needle into the Quick-Seal tube. An equal volume of water saturated isobutanol was added to the DNA, mixed by vortexing and centrifuged at 400×g for 3 minutes at room temperature to remove the ethidium bromide. This step was repeated 5 times. The DNA was dialyzed against 3 changes of TE buffer, pH 8.0, at room temperature. The DNA was extracted once with a 1:1 mixture of chloroform and phenol saturated with TE buffer, once with chloroform, precipitated with ethanol, washed with 70% ethanol, dried and dissolved in TE buffer, pH 7.6 (Godson, G. N. and D. Vapnek, Biophys. Acta. 299:516 (1973)).

Coupled in vitro Transcription/Translation of ATC5

ATC5 was cloned into the expression vector pGEM-3Z which has two promoters, T7 and SP6. pGEM-3Z-ATC5 was transcribed/translated by using the TNT coupled reticulocyte lysate system (Promega cat. # L5020) according to the manufactures instructions.

Computer Facilitated DNA and Amino Acid Sequence Analysis.

The DNA sequence was compiled on an IBM computer using GCG (Genetics Computer Group Inc.) sequence software, the program was run on the unix system at Michigan State University. The composition and the translated amino acid sequence of acetyl CoA synthetase was determined by the same program. Open reading frames of acetyl CoA synthetase sequenced fragments were obtained by using the Map soft ware. Map displays both strands of DNA sequences with a restriction map above the sequence and possible protein translations shown below. Alignments of protein sequence were determined by Bestfet software. Bestfet is a powerful software for identifying the best region of similarity between two sequences whose relationship is unknown. Optimal alignments are found by inserting gaps to maximize the number of matches using the local homology algorithm of Smith and Waterman (Smith, T. F. and M. S. Waterman, Advances in Applied Mathematics. 2:482–498 (1981)). Comparison of acetyl CoA synthetase amino acid sequence with the amino acid sequences in the database was done by using the FastA software. FastA is included in the GCG package, it answers the question "What sequences in the database are similar to my sequence?". Also, TfastA software was used to search for similarity between a query peptide sequence and any group of nucleotide sequences. TFastA translates the nucleotide sequences in all six frames before performing the comparison. It is designed to answer the question, "What implied peptide sequences in a nucleotide sequence database are similar to my peptide sequence". Map, Bestfet, FastA and TFastA softwares are all included in the GCG package.

Materials

Sodium nitroprusside, β-mercaptoethanol, ethidium bromide, dithiothreitol, dimethylformamide, Tween 20, polyethylene glycol 8,000, bromophenol blue, xylene cyanol, MOPS (3-[N-Morpholino]propanesulfonic acid), coenzyme A, goat anti-rabbit IgG, Sarkosyl, diethyl pyrocarbonate, BSA, Freund's adjuvant complete, Freund's adjuvant incomplete, Tris-HCl, and Tris base were from Sigma.

Sodium citrate, sodium acetate, potassium acetate, sodium hydroxide, ammonium acetate, potassium phosphate, EDTA, chloroform, formaldehyde, glycerol were from J. T. Baker. Magnesium sulfate, boric acid, and sodium cyanide were from Mallinckrodt. Sodium chloride, ammonium sulfate, and magnesium chloride were from Columbus Chemical Industries, Inc. Ethanol was from Quantum Chemical Corp. Triton X-100 was from Research Products International.

Cesium chloride, sodium dodecyl sulfate, guanidinium isothyocyanate, formamide, phenol, IPTG (isopropyl-β-D-thiogalactopyranoside), X-Gal (5-bromo-4-chloro-3-endolyl-β-D-galactopyranoside), AMV reverse transcriptase, $T_4$ DNA polymerase, $T_4$ DNA ligase, $T_4$ polynucleotide kinase, pancreatic DNase I, pancreatic RNase, proteinase K, restriction enzymes, pUC19, and Ampicillin were from Boehringer Mannheim.

Ficoll, oligo dT-cellulose, Sephadex G-50, Sephacryl S-400 spin columns, and pALTER plasmid were from Pharmacia. DEAE Affi-Gel Blue Gel was from Bio-Rad. DEA-cellulose, No. 1, and 3 mm Chr filter paper were from Whatman. Nitrocellulose filters were from Schleicher and Schwell.

Agarose was from Gibco (Gibco BRL, Cat. # 15510-019). Agar, bacto tryptone, and bacto yeast extract were from Difco (Difco, Cat #0127-01-7).

E. coli DH5α was from Gibco. Sodium pyrophosphate, nitroblue tetrazolium, 5-bromo-4-chloro-3-endolyl phosphate, RNasin ribonuclease inhibitor, E. coli RNase H, oligo dT primers, spermidine, HaeIII, EcoRI adaptors, λgt11, E. coli γ1090r⁻, E. coli 1089r⁻, Packgene, ProtoBlot immunological screening kit, RiboClone, and pCAT-basic were from Promega. Sequanase and deoxy and dideoxy nucleotides were from United States Biochemical Corp. (USB Cat #70770).

Results cDNA Synthesis and Library Construction

RNA Isolation and cDNA Synthesis

Mammary tissue was taken from a Holstein cow 60 days postpartum. Total RNA was isolated by the guanidinium isothiocyanate cesium chloride method. Yield of total RNA ranged from 500–700 pg per gram of frozen tissue. The integrity of total RNA was analyzed by formaldehyde gel electrophoresis (FIG. 1). No significant degradation was apparent, as judged by the equal stoichiometry between low (18S) and high (28S) molecular size RNA. By this criterion, RNA was deemed suitable for use in isolating polyadenylated poly(A)⁺ RNA.

The poly(A)⁺ RNA fraction represented 0.7 to 1.2% of the total RNA passed over the column, which is in line with the reported percentage of poly(A)⁺ RNA in higher euocaryotes. Less than 3% was isolated by this method (Aviv, H. and Leder, P. PNAS. 69:1408 (1972)).

Figure 2:
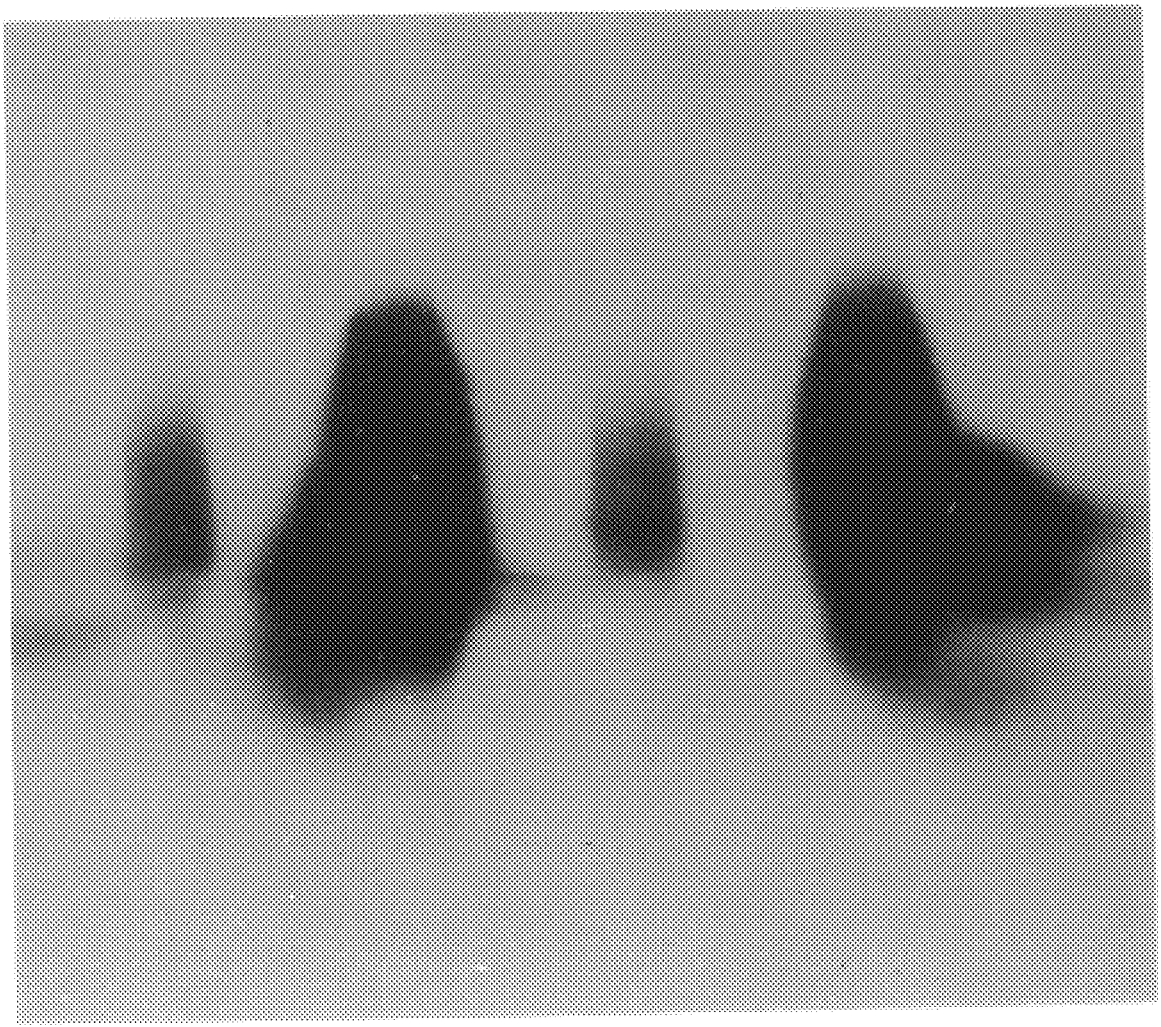
FIG. 2 is a photograph showing gel analysis of cDNA. The inset shows the successful first and second strand synthesis (lanes 2 and 4 respectively) Total RNA was used as a control (lane 1 and lane 3).
Figure 3:
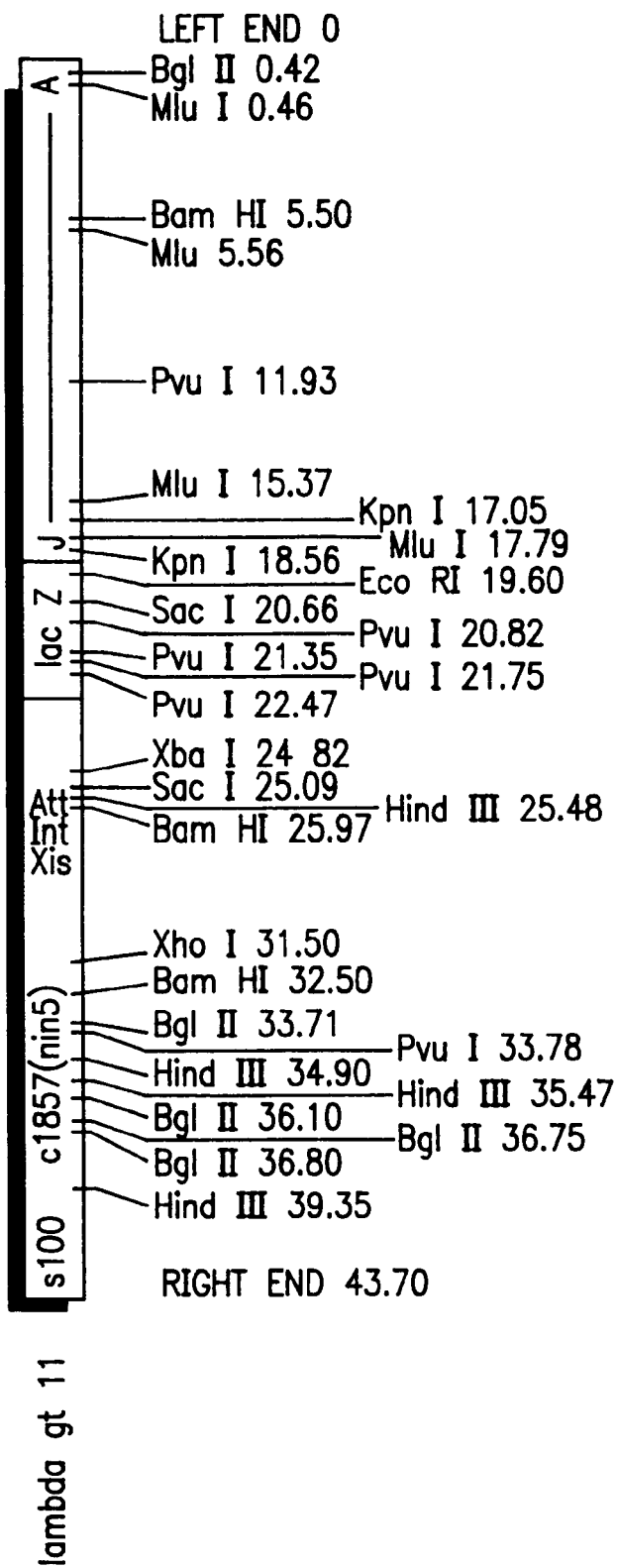
FIG. 3 is a genetic and restriction enzyme map of the phage cloning vector, λgt11.

Once enough poly(A)⁺ RNA was isolated, single and double stranded cDNA were synthesized. The reaction was carried out with 5 μg of poly(A)⁺ RNA. Five μci of [α-$^{32}$P] dCTP added to both the first and second strand synthesis reaction permitted determination of cDNA molecular size using alkaline gel electrophoresis and autoradiography (FIG. 2). An increase in density can be seen when the double stranded cDNA (lane 2) is compared to the single stranded cDNA (lane 1). The majority of double stranded cDNA was between 0.3 and 4.5 kb in size. This range was satisfactory since native acetyl-CoA synthetase has a molecular weight of 63 kD; therefore, its predicted mRNA size should be on the order of 2 kb. The cDNA was blunt-ended and synthetic EcoRI adapters were attached. Separation of free adapters from the cDNA was achieved by sephacryl-S 400 column chromatography. cDNA fragments greater than 400 bases in length were isolated. The purified cDNA was ligated into a unique EcoRI site contained in the phage expression vector λgt11 (FIG. 3) (Young, R. A. and R. W. Davis, Proc. Natl. Acad. Sci. 80:1194 (1983)). Thus, the Holstein mammary acetyl-CoA synthetase cDNA was inserted into the λgt11 lacZ gene, coding for β-galactosidase, at the EcoRI site.

λgt11 was chosen because libraries constructed in this vector can be screened with nucleic acid hybridization probes or with antibodies directed against the protein of interest. Also, since genes cloned into λgt11 can be expressed as β-galactosidase fusion protein or, in some cases, as non-fusion protein, it is often possible to measure the activity of an expressed protein in recombinant λgt11 lysogenies.

Figure 4:
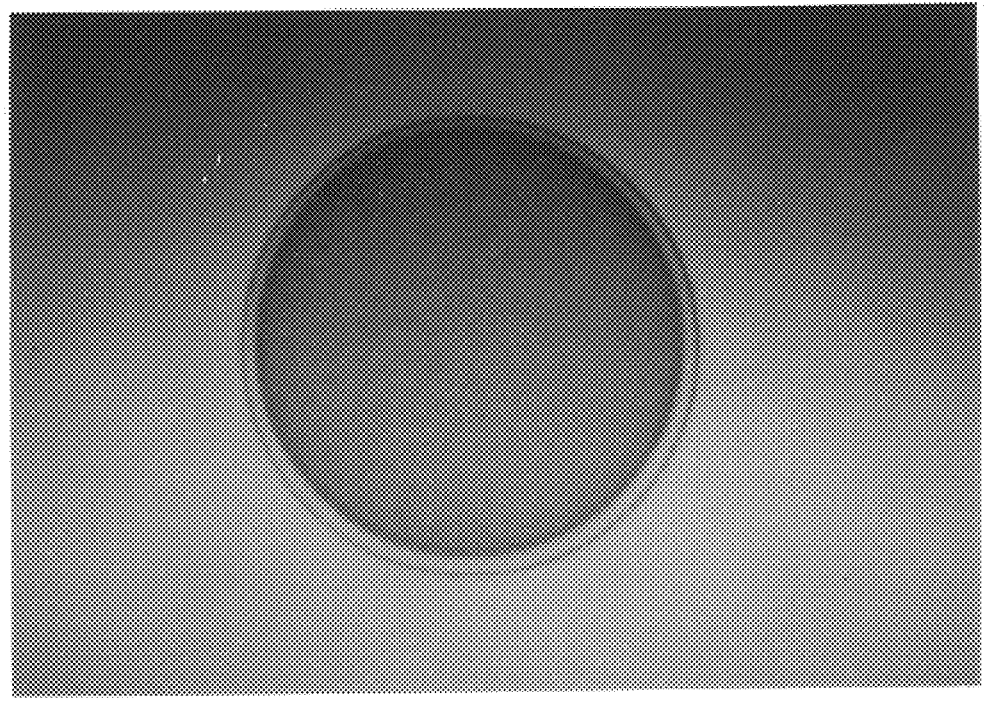
FIG. 4 is a photograph showing E. coli (Y1090) infected with Holstein mammary gland cDNA library plated on agar plate, containing, ampicillin, IPTG, and x-gal. The plates showed 50 to 60% recombinant colonies (clear).

Recombinant phage was packaged into phage heads with one packaging reaction. The packaged phage was infected into E. coli Y1090 cells and tittered. Total number of recombinant phage was greater than $2\times10^6$ plaque forming units (pfu) before library amplification. Average recombinant frequency was between 50–60% (FIG. 4). The abundance of acetyl-CoA synthetase mRNA species in the poly (A)⁺ RNA fraction was unknown at this point. Assuming that the message level was equivalent to the acetyl-CoA synthetase protein level in mammary total protein extract (approximately 0.001%) (Cook, R. M. et al., Agr. and Food Chem. 23:561–563 (1975)), a cDNA library containing $2\times10^7$ recombinant plaques before amplification would be expected to contain a maximum of 200 plaques of the acetyl-CoA synthetase cDNA. Even if this assumption was in error by two orders of magnitude, one could still reasonably expect to isolate an acetyl-CoA synthetase cDNA from a library of this size.

Figure 5:
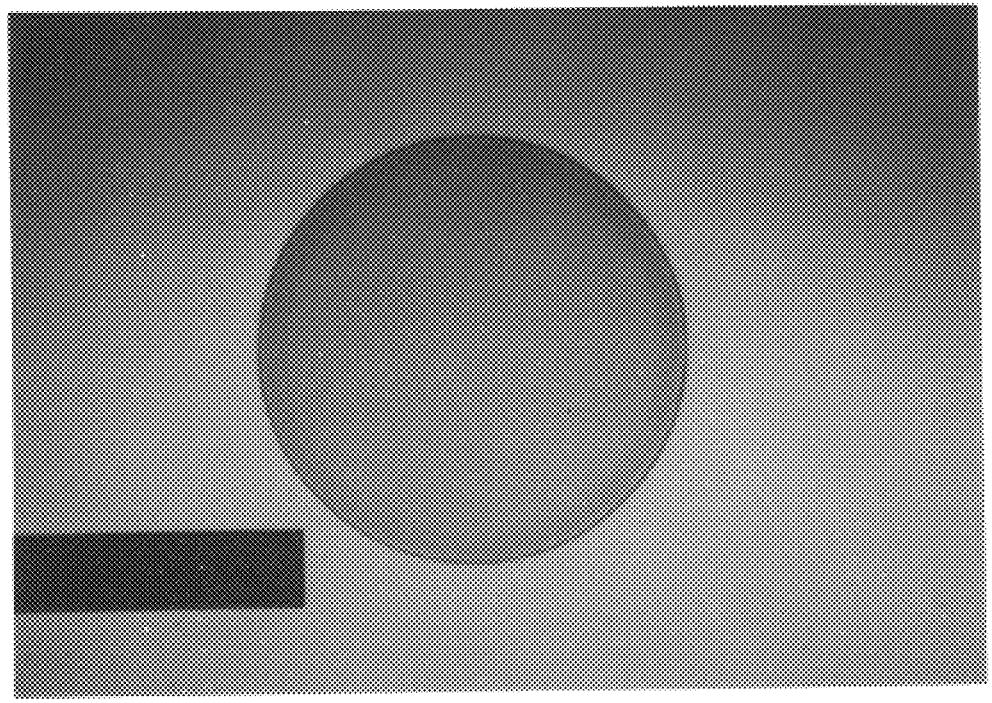
FIG. 5 is a photograph showing purification of λgt11-AR8. E. coli (Y1090) was infected with λgt11-AR8 and plated on agar plates containing ampicillin, IPTG, and x-gal. All plaques were clear indicating 100% recombinant λgt11.
Figure 6A:
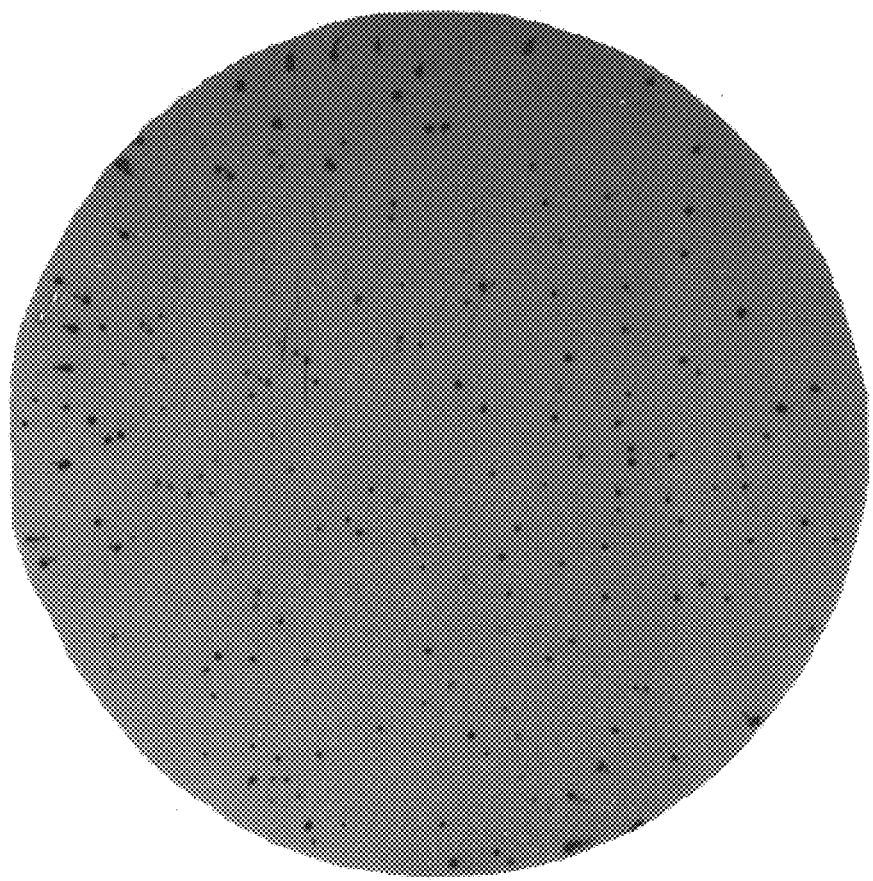
FIGS. 6A and 6B are a photographs showing a representative primary screen of Holstein mammary gland cDNA library. Filters were lifted from plates containing 200 plaques and were screened with rabbit anti-bovine acetyl-CoA synthetase. Positive signals (λgt11-AR8) are shown on filter A, and false positive signals (λgt11) are shown on filter B.
Figure 6B:
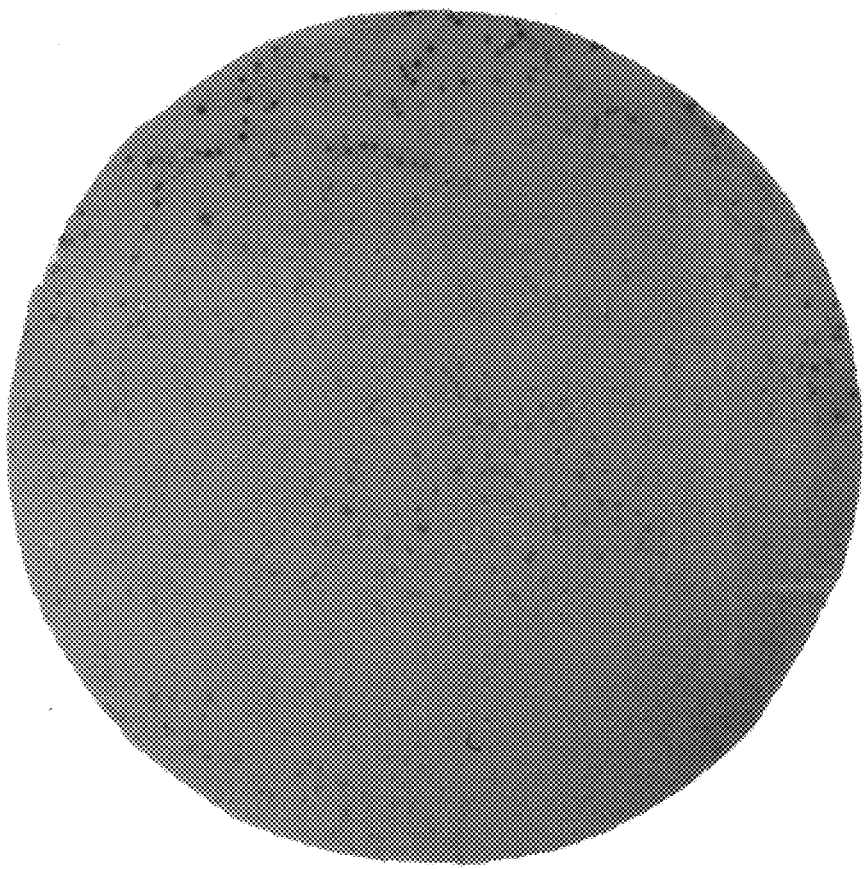

Isolation and characterization of a positive plaque from the bovine λgt11 library Immunological screening The bovine mammary gland cDNA library was screened using rabbit anti-bovine acetyl-CoA synthetase. Twelve positive colonies were observed out of $6\times10^5$ plaques. Rescreening of the 12 clones with the same antibody at plaques. Rescreening of the 12 clones with the same antibody at a low pfu density (about 200 plaques/plate) revealed one positive plaque. This plaque was designated λAR8, the plaque was recombinant (FIG. 5). During primary screening, the color of the false positive signals was observed to be weaker than that of the positive one (FIGS. 6A and 6B). This phenomena may be caused by the nonspecific binding of the antibody and bacterial proteins. To minimize this the rabbit antiserum was pretreated with E. coli protein extract.

Phage DNA mini-preps were performed on each clone and the purified phage DNA was subjected to EcoRI restriction analysis to determine the cDNA insert size. The fragments were separated by agarose gel electrophoresis. Colony λAR8-ACS contained a 200 bp cDNA fragment (FIG. 7).

Studies performed on λAR8

To determine if λAR8 cDNA fragment can be used to screen the bovine mammary library, it was amplified and subjected to enzyme assay, Southern blot analysis and DNA sequencing.

Acetyl-CoA synthetase activity in λAR8 fusion protein

When the recombinant λgt11 infects its host cell, the ACS-β-galactosidase fusion protein, the product of the recombinant lacZ gene is synthesized.

Acetyl-CoA synthetase activity was measured in 5 μg of fusion protein produced from E. coli 1089 infected with wild-type λgt11 and with λAR8. Also, these fusion proteins were treated with the rabbit anti-bovine acetyl-CoA synthetase antibody and with anti β-galactosidase monoclonal antibody. Enzyme activity was 29% higher in the λAR8 fusion protein as compared to the λgt11 fusion protein. Acetyl-CoA synthetase-specific activity decreased by 35% and 100% when the recombinant λAR8-ACS fusion protein was treated with rabbit anti-bovine acetyl-CoA synthetase or β-galactosidase monoclonal antibody, respectively (Table 1).

TABLE 1

Acetyl-CoA synthetase activity in the fusion protein of λgt11-AR8

| Extract | Standard | Test | Δ O.D. | ACS specific activity |
|---|---|---|---|---|
| *Without antibody* | | | | |
| E. coli (1089) | 0.361 | 0.331 | 0.030 | 19.4 |
| λgt11 | 0.354 | 0.316 | 0.038 | 24.6 |
| λAgt11-AR8 | 0.355 | 0.307 | 0.048 | 31.1 |
| *With rabbit anti-bovine ACS* | | | | |
| E. coli (1089) | 0.357 | 0.326 | 0.031 | 20.0 |
| λgt11 | 0.354 | 0.315 | 0.039 | 25.3 |
| λgt11-AR8 | 0.341 | 0.341 | 0.017 | 11.0 |
| *With monoclonal β-galactosidase antibody* | | | | |
| E. coli (1089) | 0.352 | 0.321 | 0.031 | 20.0 |
| λgt11 | 0.348 | 0.310 | 0.038 | 24.6 |
| λgt11-AR8 | 0.335 | 0.336 | 0.00 | 0.00 |

\* *E.coli* is fusion protein extract of *E. coli*; λgt11, is fusion protein extract of *E.coli* infected with wild type λgt11; λgt11-AR8 is fusion protein extract of *E. coli* infected with λAR8-ACS.
\* One unit of enzyme activity is defined as 1 μmol of substrate reacting per hour.
\* The results are averages of duplicate determinations for each of the three independent experiments.

On the other hand, neither rabbit anti-bovine acetyl-CoA synthetase or β-galactosidase monoclonal antibody affected the enzyme activity of λgt11 fusion protein. Protein A-positive *S. aureus* cells was used as second antibody.

Southern blot analysis

A. Probing of fungal ACS DNA with λAR8

An *N. crassa* acetyl-CoA synthetase gene was generously provided by Dr. Connerton (Connerton, I. F., et al, Mol. Microbiol. 4:451–460 (1990)). *N. crassa* acetyl-CoA synthetase gene is 6 kb, it is cloned in pEMBL 8 vector in Hind III restriction sites. *N. crassa* DNA was digested with HindIII. The fungal acetyl-CoA synthetase DNA was separated in 0.8% agarose gel and transferred to a nitrocellulose filter. This membrane was probed with λAR8 cDNA fragment. The wash conditions were 0.3×SSC, 0.1% SDS at 55° C. λAR8-ACS bound to the fungal acetyl-CoA synthetase gene (FIG. 8).

B. Genomic Southern blot analysis

Bovine genomic DNA was digested with EcoRI and separated by agarose gel electrophoresis. A Southern blot of this gel was then probed with the λAR8 cDNA fragment (200 kb). The filter was washed 15 minutes with 0.3×SSC, 0.1% SDS at 55° C. Autoradiography showed one band (FIG. 9).

Sequence of the λAR8 cDNA

Figure 10:
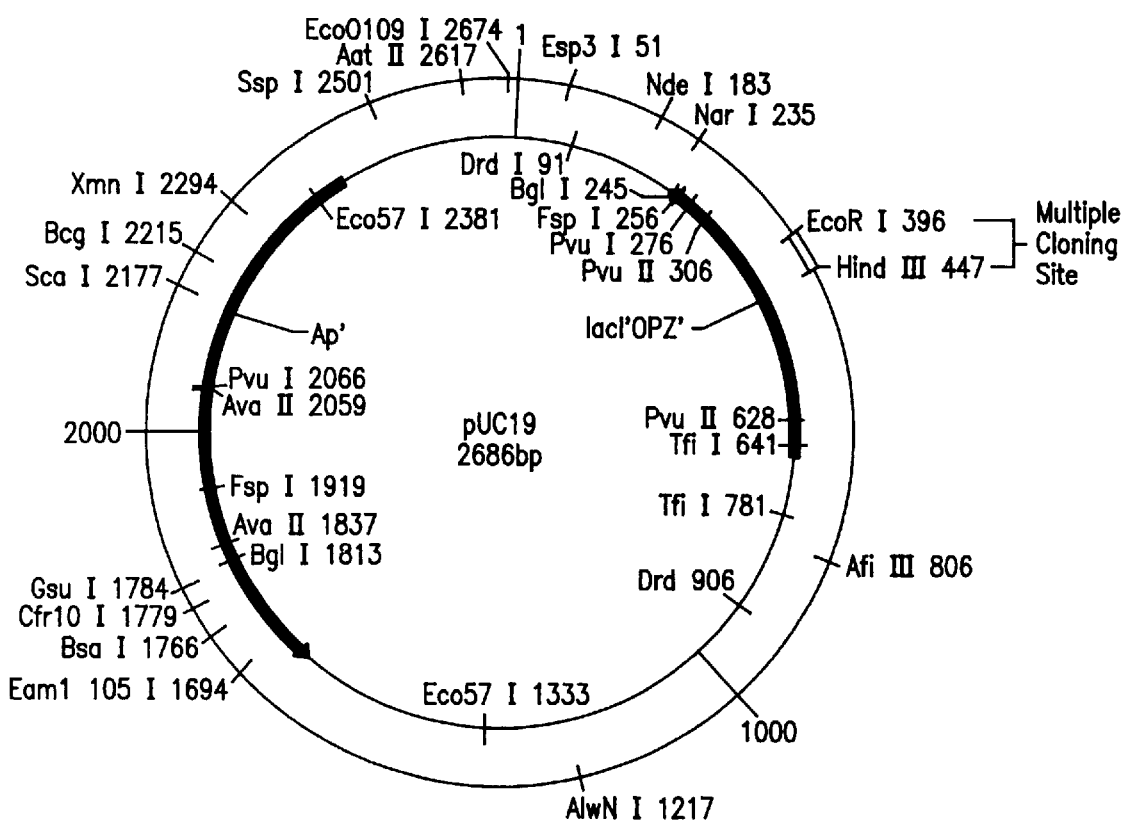
FIG. 10 is a genetic and restriction enzyme map of the phage cloning vector, pUC19.
Figure 11:
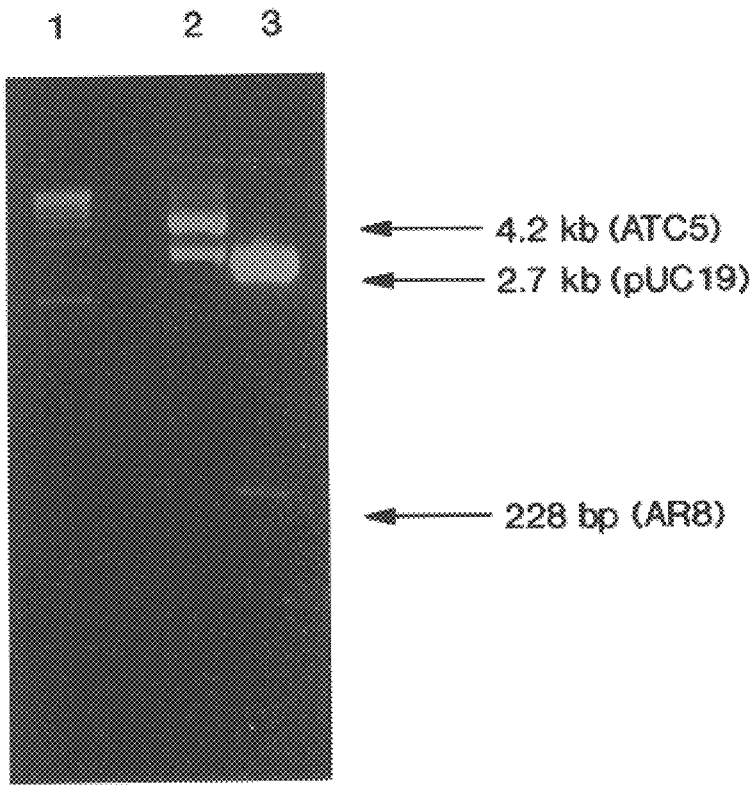
FIG. 11 shows an examination of AR8 and ATC5 cloned in pUC19 on a photograph. AR8 and ATC5 were cut from λgt11, separated in agarose gel, eluted and cloned into pUC19. A DNA mini-prep was prepared using positive colonies and DNA was cut using EcoRI. The inset shows-:lane 1, DNA standard; Lane 2 pUC19-ATC5 digest; and lane 3, pUC19-AR8 digest.

The positive recombinant clone (λAR8) containing Holstein mammary acetyl-CoA synthetase cDNA, judged by antibody screening, Southern blot and enzyme assay was amplified, and the recombinant λgt11 DNA was purified (see materials and methods). The purified DNA was digested with EcoRI and the DNA fragments were separated in agarose gel (FIG. 7). The 200 bp fragment was subcloned into a pUC19 vector (FIG. 10) at the EcorI site, and insertion was confirmed by EcoRI digestion of the recombinant pUC19-AR8 DNA and agarose gel analysis (FIG. 11). The corresponding double stranded pUC19-AR8 DNA was sequenced in both directions by using the dideoxy chain termination method (Sanger, et al., Proc. Natl Acad. Sci. 74:5463 (1977)). The universal primer was used to prime the sequencing reaction. Sequencing analysis showed that λAR8 DNA is 228 bp (FIG. 12). Homology search in the gene bank revealed that, AR8 has no homology with common proteins, instead AR8 showed homology (14–24%) to the ATP using enzymes.

Screening of the cDNA library with α-$^{32}$P labeled AR8

Figure 13:
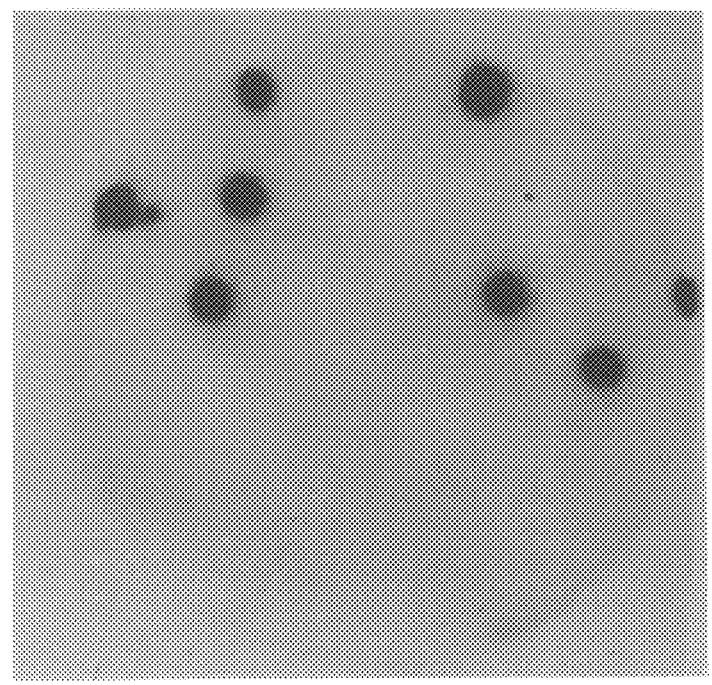
FIG. 13 is a photograph showing screening of λgt11 library with $\alpha^{32}$p AR8. Filters were lifted from plates containing 200 plaques. Positive plaques are shown on each filter.
Figure 14:
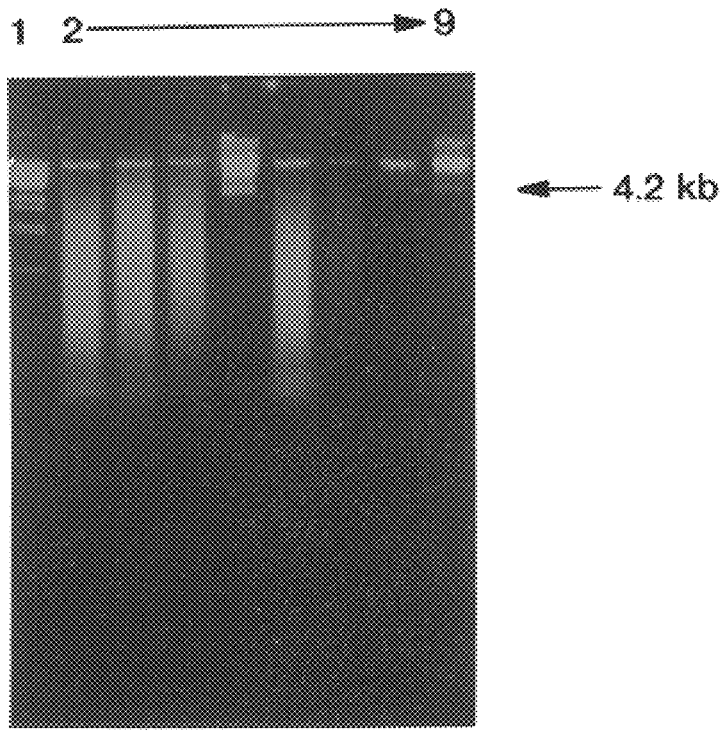
FIG. 14 is a photograph showing isolation of ACS recombinant λgt11. λgt11 containing ATC5 was purified with PEG and centrifuged using a glycerol gradient. The DNA was digested with EcoRI and separated using 0.8% agarose gel electrophoresis. The inset shows marker, lane 1; and λgt11-ATC5 lane 2 to 9.
Figures 15A, 15B:
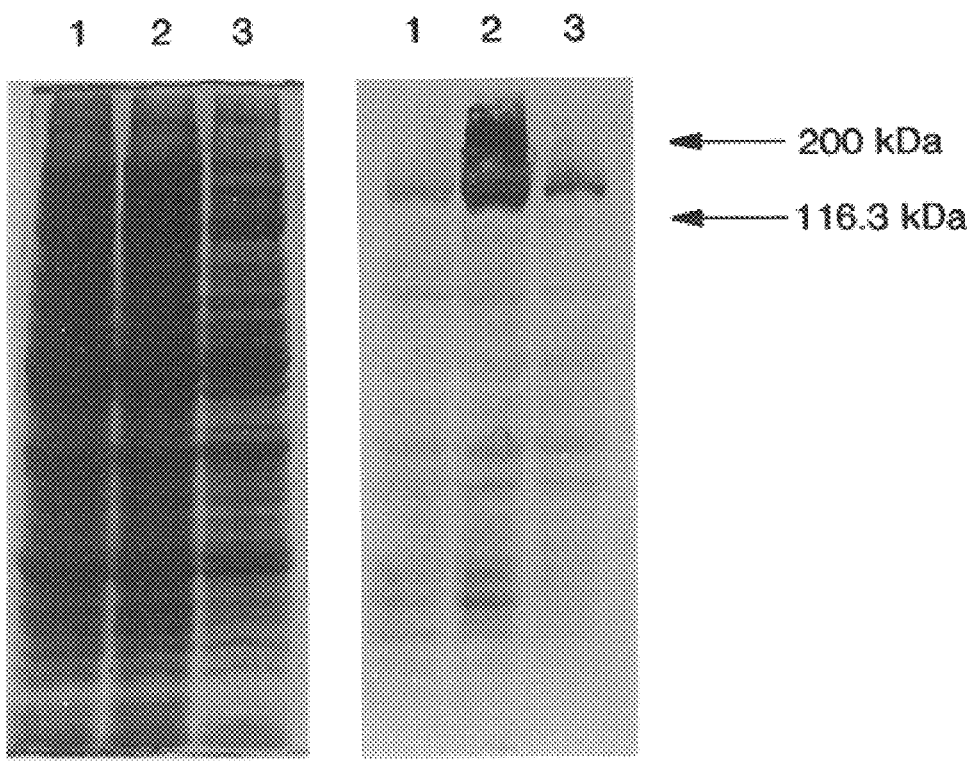
FIGS. 15A and 15B are photographs of a Western blot of ATC5 fusion protein. Panels A and B were detected with Coomaise Brilliant Blue, and antibody against β-galactosidase, respectively. Protein standard is in Panel A lane 1. The second band from the top is β-galactosidase. In Panel A, and B lane 2, E. coli Y1089 extract; lane 3, E. coli Y1089 lysogen extract (ATC5 fusion protein); lane 4 E. coli Y1089 lysogen (λgt11 fusion protein).

The mammary gland bovine library was rescreened by plating 1×10$^6$ recombinant phage plaques which were transferred to nitrocellulose filters and hybridized to the 228 bp EcoRI restriction fragment of AR8 (FIG. 13). Twenty eight positive plaques were isolated. These plaques were plaque purified, by several rounds of screening. Phage DNA mini preps were performed for all 28 of the purified colonies and the isolated DNA was digested with EcoRI. Analysis of the digests by agarose gel electrophoresis, revealed that 9 colonies had an insert of 4.2 kb (FIG. 14). This phage was selected for further study and designated λATC5. This 4.2 fragment was subcloned into pUC19 vector (pUC19-ATC5) at the EcoRI site, and insertion was confirmed by EcoRI digestion of the recombinant pUC19-ATC5 DNA and agarose gel analysis (FIGS. 15A and 15B).

λATC5 fusion protein enzyme assay

Fusion protein was prepared from λATC5-ACS and wild type λgt11, as described "in materials and methods." Again the fusion protein was treated with either rabbit anti-bovine acetyl-CoA synthetase polyclonal antibody or with β-galactosidase monoclonal antibody. Acetyl-CoA synthetase fusion protein specific activity increased 93% in the λATC5 fusion protein compared to λgt11 fusion protein (control). In addition, acetyl-CoA synthetase-specific activity decreased by 85% and 50% when the fusion protein was treated with anti β-galactosidase and the rabbit anti-bovine acetyl-CoA synthetase (Table 2).

TABLE 2

Acetyl-CoA synthetase activity in the fusion protein of λgt11-ATC5

| Extract | Standard | Test | Δ O.D. | ACS specific activity |
|---|---|---|---|---|
| *Without antibody* | | | | |
| E. coli (1089) | 0.317 | 0.244 | 0.073 | 28.8 |
| λgt11 | 0.317 | 0.277 | 0.040 | 23.9 |
| λgt11-ATC5 | 0.317 | 0.210 | 0.107 | 46.1 |
| *With rabbit anti-bovine ACS* | | | | |
| E. coli (1089) | 0.273 | 0.228 | 0.045 | 18.7 |
| λgt11 | 0.273 | 0.223 | 0.050 | 22.7 |
| λgt11-ATC5 | 0.273 | 0.219 | 0.054 | 23.1 |
| *With monoclonal β-galactosidase antibody* | | | | |
| E. coli (1089) | 0.302 | 0.252 | 0.050 | 19.4 |
| λgt11 | 0.302 | 0.262 | 0.030 | 21.6 |
| λgt11-ATC5 | 0.302 | 0.242 | 0.040 | 7.00 |

\* *E.coli* is fusion protein extract of *E. coli*; λgt11, is fusion protein extract of *E.coli* infected with wild type λgt11; λgt11-ATC5 is fusion protein extract of *E. coli* infected with λATC5-ACS.
\* One unit of enzyme activity is defined as 1 μmol of substrate reacting per hour.
\* The results are averages of duplicate determinations for each of the three independent experiments.

However, rabbit anti-bovine ACS and β-galactosidase treated λgt11 fusion protein did not show change in activity.

Immunoblot analysis of ATC5 fusion protein

Positive plaque ATC5 was further analyzed by western blotting of the acetyl CoA synthetase-β-galactosidase fusion protein produced by this plaque (FIGS. 15A and 15B). Bands in panel A were visualized by Coomassie blue staining, while the bands in panel B were visualized by treating with the anti-β-galactosidase antibody (FIGS. 15A and 15B). The recombinant λgt11 fusion protein showed two bands, 180 and 116 kD (lane 2 in panel B), and the nonrecombinant λgt11 fusion protein showed one band, 116 kD (lane 3 in panel B). λgt11, and nonrecombinant λgt11.

Southern blot analysis of λATC5 DNA

Figure 16:
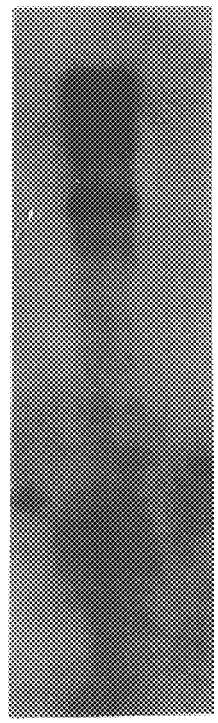
FIG. 16 is a photograph of a Southern blot analysis of bovine genomic DNA probed with $\alpha^{32}$P-ATC5. Genomic DNA was digested with HindIII and EcoRI. DNA was separated in agarose gel. The results indicate one gene copy of acetyl-CoA synthetase.

Bovine genomic DNA was digested with EcoRI and subjected to agarose gel electrophoresis. A Southern blot of this gel was then probed with λATC5 cDNA fragment. The filter was washed for 15 minutes with 0.3×SSC, 0.1% SDS at 55° C. The autoradiography showed one band (FIG. 16). Band size was the same as that detected using AR8.

Figure 17:
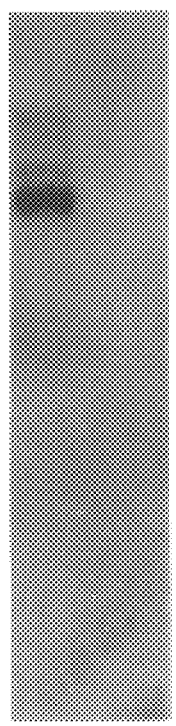
FIG. 17 is a photograph of a Southern blot of N. crassa acetyl-CoA synthetase probed with $\alpha^{32}$P-ATC5. The fungal clone was digested with HindIII. DNA was separated in agarose gel. The results indicates that AR8 is homologous to the fungal acetyl-CoA synthetase gene.

Another Southern blot of *N. crassa* ACS DNA was prepared and probed with λATC5 cDNA fragment. λATC5 cDNA bound to the *N. crassa* acetyl-CoA synthetase gene (FIG. 17).

Northern blot analysis of mRNA from bovine tissue

Figure 18:
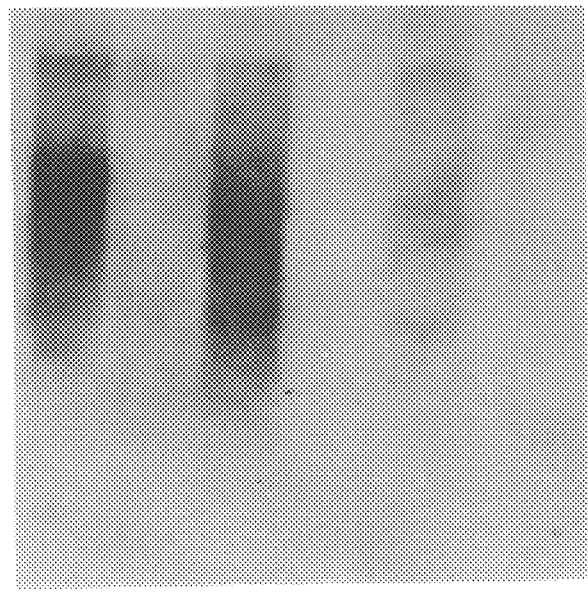
FIG. 18 is a photograph of Acetyl-CoA synthetase mRNA multiple forms in different Holstein tissues. poly(A$^+$) RNA from different Holstein tissues was isolated, separated in formaldehyde gel, transferred to nylon membrane and probed with α32P ATC5. Five λg of poly(A$^+$)RNA were used in each lane. Lanes: 1, heart; 2, liver; 3, mammary gland and 4, kidney. Heart has 3, mammary gland 3, kidney 2, and liver 1 form of acetyl-CoA synthetase mRNA. The mRNA population ranged from 5.2 to 0.8 kb.

To determine the size of acetyl-CoA synthetase mRNA. A northern blot of [poly(A$^+$)] RNA from Holstein heart, liver, kidney and mammary gland was hybridized with ATC5 cDNA fragment. To increase the band intensity the probe was labeled with both α-32P dCTP and α-$^{32}$P dATP. Surprisingly, different species of mRNA were detected in different tissues (FIG. 18). The number of acetyl-CoA synthetase mRNA bands found was 3, 1, 2 and 4 for heart, liver, kidney and lactating mammary gland, respectively. The multiple forms of ACS mRNA ranged from 0.8 to 5.2 kb.

Slot blot Analysis of ACS mRNA

To investigate the effect of lactation on acetyl-CoA synthetase mRNA levels, [poly(A$^+$)] RNA was isolated from a dry, and 60, 120 and 180 days postpartum mammary gland tissue. A slot blot of these mRNA was probed with ATC5 cDNA fragment (FIGS. 19A and 19B). The filter was washed for 15 minutes with 0.3×SSC, 0.1% SDS at 55° C. Acetyl-CoA synthetase mRNA increased 3 folds, at 120 days postpartum comparing to 60 and 180 days of lactation. However, in the dry mammary gland acetyl-CoA synthetase level was very low, as determinant by densitometer. This experiment demonstrates that the gene is not transcribed in the dry mammary gland. On the other hand, mammary acetyl-CoA synthetase gene transcription increases to a maximum at 120 days of lactation and declines as lactation advances. This agrees with the measurement of enzyme activity during lactation. This data suggests that this gene is controlled at the transcription level.

Antibody studies

A. Western blot analysis

Figure 21:
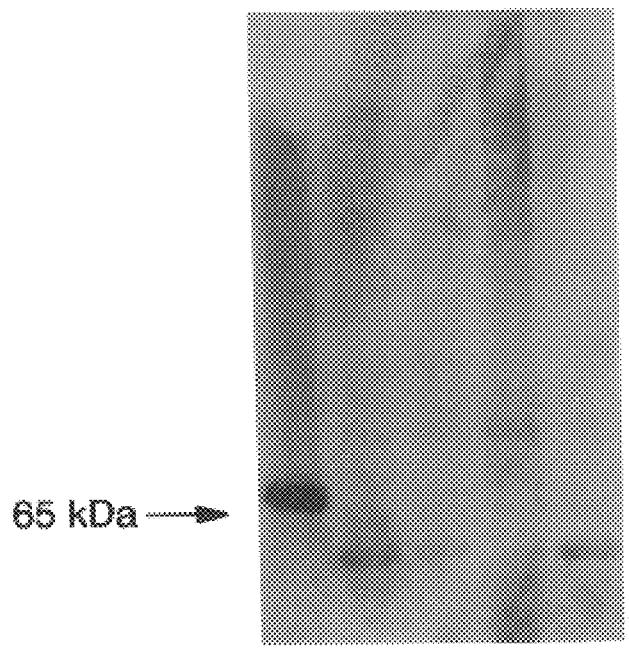
FIG. 21 is a photograph of a Western blot analysis of mitochondrial extract, examined with rabbit anti-bovine acetyl-CoA synthetase antibody purified using the ATC5 fusion protein. Mitochondrial proteins were separated in 12.5% SDS-polyacrylamide gel. Also, rabbit anti-acetyl-CoA synthetase was purified. Alkaline phosphatase-conjugated goat anti-rabbit IgG was used as second antibody. Twenty µg of protein was used for each extract. lanes: 1, spleen; 2, kidney; 3, mammary gland; 4, liver; and 5, heart. Accordingly, the antibody against Holstein mammary acetyl-CoA synthetase has a reasonably high specificity.

To verify that the polyclonal antibody used to screen the library detects acetyl-CoA synthetase, and to investigate the expression of the ACS gene in different tissue, a series of western blot analyses were undertaken. Western blot of mitochondrial protein extracts from heart, liver, kidney, mammary gland and spleen, were treated with polyclonal rabbit anti-bovine acetyl-CoA synthetase and then with goat anti-rabbit alkaline phosphatase-conjugated IgG (FIG. 20). The acetyl-CoA synthetase polyclonal antibody used in this experiment has nonspecific reactivity (FIG. 20) with other proteins. Therefore, this polyclonal antibody, was purified by incubating with the acetyl-CoA synthetase fusion protein produced by λATC5. This purified antibody was used again in a western blot analysis of mitochondrial extracts from liver, heart, mammary gland, kidney and spleen (FIG. 21). The purified antibody bound to one band in heart, kidney and mammary gland tissue with apparent molecular weight of 65 kD. For spleen tissue, however, the band size was 78 kD, and there was no binding to the liver protein extract. Consequently, this demonstrates that the immunological screening of the λgt11 library detected ACS. In addition, acetyl-CoA synthetase gene is expressed in heart, kidney and mammary tissue, but not in liver. For spleen the band at 78 kD is unexplained.

Tissue extract enzyme assay

Rabbit anti-ACS used in the immunological screening of λgt11 library was affinity purified using the fusion protein produced by λATC5-ACS. This antibody was then shown to remove 90% of acetyl-CoA synthetase activity from the preparation of partially purified Holstein heart acetyl-CoA synthetase (Table 3).

TABLE 3

Effect of purified rabbit anti-bovine ACS antibody on heart ACS activity

| Antibody | Standard | Test | Δ O.D. | ACS specific activity |
|---|---|---|---|---|
| None | 310 | 286 | 24 | 31 |
| Second | 310 | 287 | 22 | 29 |
| First and second | 310 | 301 | 8 | 10 |

\* The first antibody was rabbit anti-ACS affinity purified using the fusion protein produced by λgt11-ATC5. The second antibody was goat anti-rabbit IgG.
\* The results are averages of duplicate determinations.

Accordingly, the purified antibody is highly specific for acetyl-CoA synthetase.

Restriction map

Figure 22A:
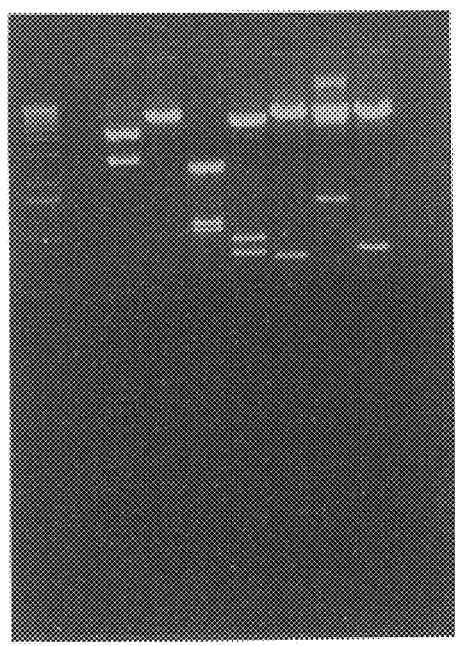
FIGS. 22A and 22B are graphs of single and double restriction digests of pUC19-ATC5. pUC19-ATC5 DNA was prepared and digested with several 6 bp cutters. Panel A shows DNA standard; EcoRI; BamHI; BglI, PvuI, SalI, ScaI and SspI digests in lanes 1 to 8, respectively. Panel B shows DNA standard in lane 1 and double digests of pUC19-ATC5 by BglI-EcoRI, BglI-ScaI, BglI-SspI and BglI-SalI are, in lanes 2, 3, 4 and 5, respectively.
Figure 22B:
Figure 23:
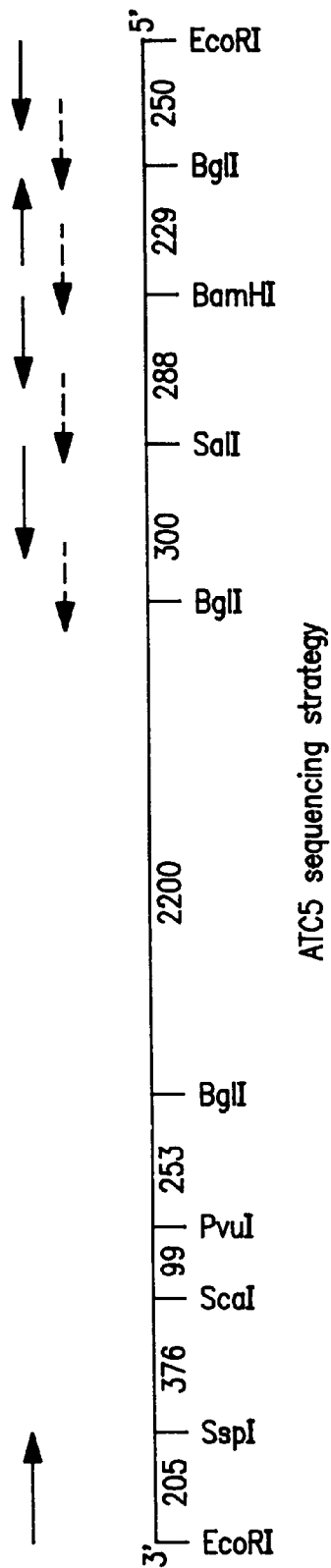
FIG. 23 shows restriction map and sequencing strategy of ATC5. Restriction sites were determined by single and double endonucleolytic digestions. pUC19-ATC5 was digested with BamHI and SalI. Subclones of the cDNA and the direction in which they were sequenced are given by arrows below the map. The dotted arrows represent the location and the direction of the oligos used to sequence the overlap.

The partial restriction map of pUC19-ATC5 is presented in FIG. 23. To determine restriction sites, restriction enzymes that recognize 6 bp sequence, which theoretically occurs every 4096 bp were used. Therefore a 6 bp cutter would cut ATC5 once. To determine the exact site of each restriction enzyme, pUC19-ATC5 was first cut with a single restriction enzyme then with two restriction enzymes at the same time (FIGS. 22A and 22B).

In vitro transcription\translation of ATC5

Figure 24:
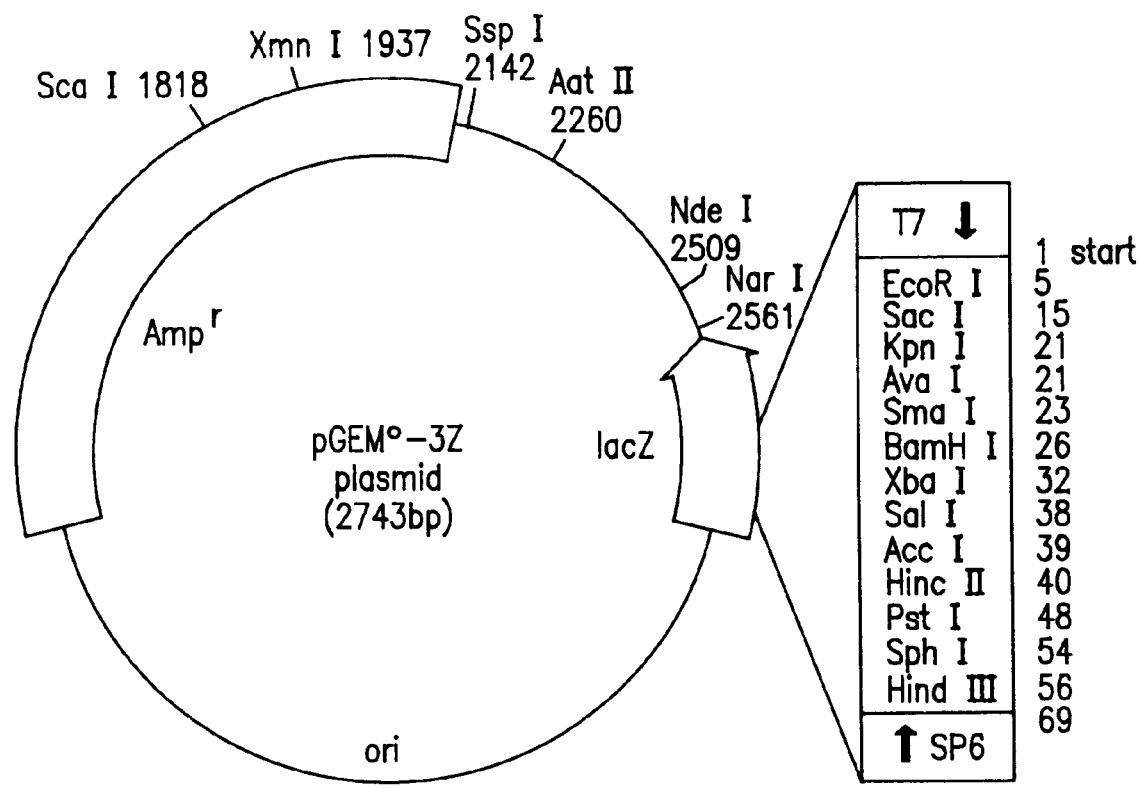
FIG. 24 is a genetic and restriction enzyme map of the plasmid cloning vector pGEM-3Z.
Figure 25:
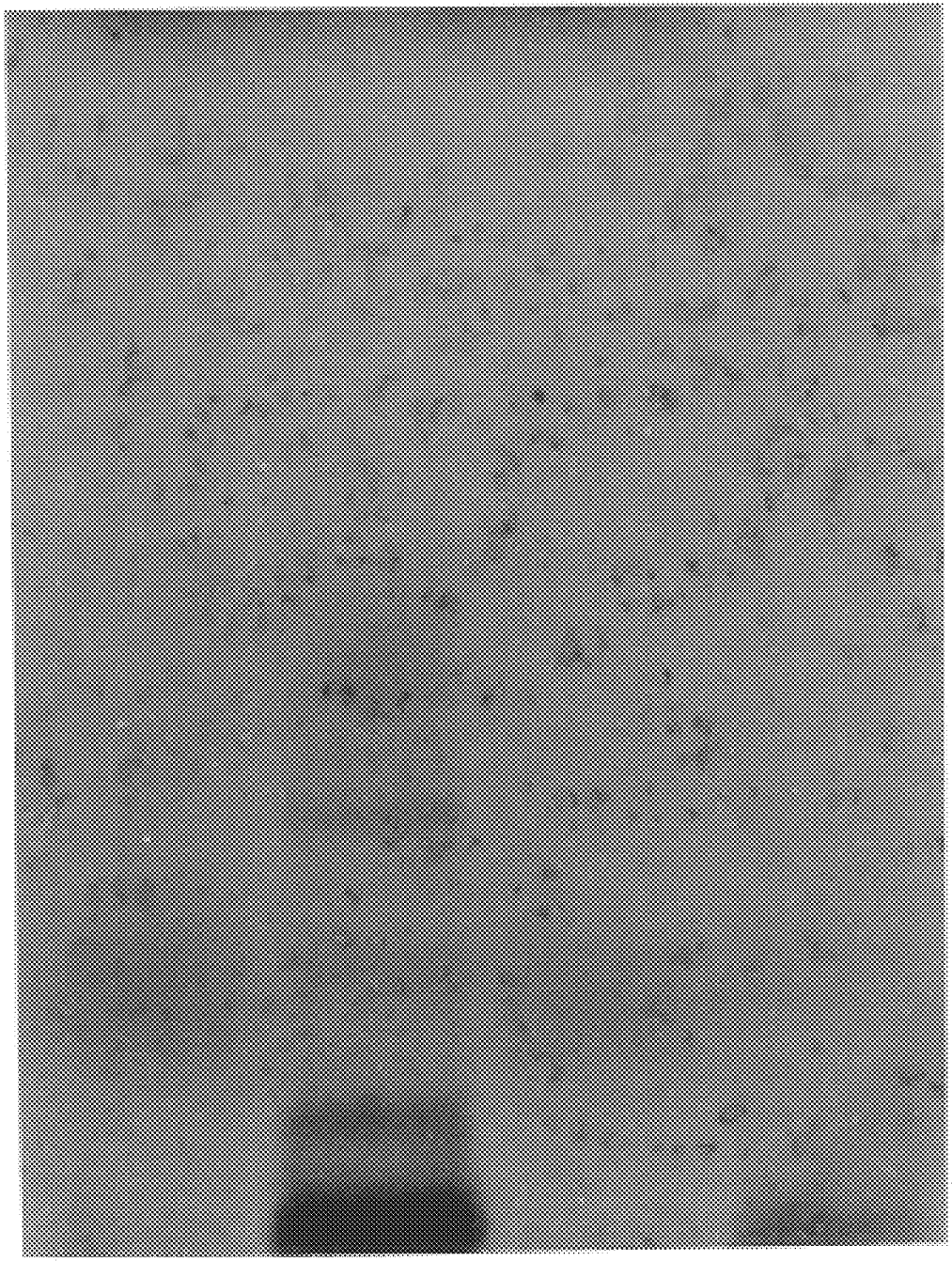
FIG. 25 is a photograph showing in vitro translation of ATC5. T7 and SP6 promoters were activated individually. Lane 1, pGEM-3Z (control); lane 2, T7; lane 3 SP6 activation products. Activation of T7 resulted in protein synthesis while activation of SP6 did not.

The initial plasmid construct was derived by subcloning the λgt11-ATC5 4.2 kb EcoRI fragment into the EcoRI site of the pGEM-3Z vector (FIG. 24). Plasmid DNA mini preps were prepared to select the pGEM-3Z-ATC5 clone. To confirm the presence of ATC5 pGEM-3Z-ATC5 DNA was subjected to EcoRI digestion and the fragments separated by agarose gel electrophoresis. pGEM-3Z is designed to allow transcription by T7 and SP6 polymerase. Activation of both promoters was carried on separately. The activation of T7 resulted in production of a protein (55 kD), while the activation of SP6 did not (FIG. 25).

Partial sequencing and analysis of ATC5

In the pUC19-ATC5 construct, the universal primer was used to prime the sequencing reaction. Four oligonucleotide sequencing primers were synthesized to sequence the overlaps. As such, a fragment of 1130 bp starting at the 5' end, was completely sequenced in one direction (5'→3') and 216 bp were sequenced at the 3' end (3'→5'). The sequencing strategy used to sequence the pUC19-ATC5 is shown in FIG. 23.

Analysis of the completed sequence data by the GCG DNA software revealed additional genetic elements, including the location of the restriction enzyme sites, a possible open reading frame (ORF), and a possible transcription start codon (FIGS. 26A-1 and 26A-2). With respect to six base restriction sites, 34 restriction enzyme sites were found: 11 are unique sites, and 23 are duplicated sites. A map of these sites and their relative positions in the cDNA sequence is shown in FIGS. 26A-1 and 26A-2.

Acetate is a major substrate for milk synthesis. The metabolic form of acetate is acetyl-CoA. The mechanism for generating acetyl-CoA is the acetate activating reaction catalyzed by acetyl-CoA synthetase (ACS). Our laboratory has determined ACS tissue distribution, intracellular localization, physical and catalytic properties, and changes in activity in mammary gland has been determined throughout lactation. Molecular studies were the next extension of this work to further understanding of acetyl-CoA synthetase. Specifically, the objective of this invention was to clone bovine ACS and characterize the cDNA encoding ACS.

The ACS cDNA

The ACS cDNA has a continuous ORF, beginning at the 5' terminus and continuing for 323 amino acid residues. Obviously the cDNA can not be judged to be full length depending on a partial sequence. However, several observations indicate that the λgt11-ATC5 codes for the full-length ACS protein. The first observation revolves around the size of the fusion protein. The fusion protein will have a higher molecular weight than that of wild type λgt11 β-galactosidase and react with the β-galactosidase antibody. Indeed, immunoblotting analysis of the fusion protein gave these results (FIGS. 15A and 15B). Thus, it can be seen that the fusion protein which has a molecular weight of 180 kD is 63 kD larger than λgt11 β-galactosidase (116.3 kD) and reacts with anti-β-galactosidase. In contrast, $E.$ $coli$ Y1089 (control) show no bands corresponding to the fusion protein. Therefore, the western blot analysis of the fusion protein presents strong evidence that ATC5 is a full length cDNA.

Another observation which may offer evidence to support the full-length character of ACS cDNA concerns the size of the native and in vitro translated acetyl-CoA synthetase. The molecular weight of the product of transcribed\translated pGEM-3Z-ATC5 gene is slightly smaller (8 kD) than the molecular weight of the native protein. The in vitro translation system is a cell free system. Therefore, glycosylation is not expected to take place in this reaction. The native protein was reported to contain more than 0.7% carbohydrate by weight, such as N-acetylneuraminic acid, fucose and glucose (Stamoudis, V. and R. M. Cook, J. Agric. Food Chem. 23:563 (1975)). Due to the lack of a glycosylation system the in vitro translated protein would have a lower molecular weight than the native protein. SDS-PAGE analysis showed this difference, (FIG. 21 and FIG. 25). In addition a western blot of mitochondrial extracts from several ruminant tissues demonstrated that rabbit anti-bovine ACS bound to 63 kD protein. However, the size of recombinant ACS is 55 kD. If a significant amount of N-linked suger is present on the native protein, a minimum increase of 2.5 kD should be expected and would be detected by these methods (Mayes and Waterfield, EMBO J.,3:531–7 (1984). The fact that the two proteins have different molecular weight supports glycosylation of the native enzyme.

Finally, the enzymatic activity of both recombinant and native ACS provides strong evidence that ACS cDNA is a full length transcript. Recombinant ACS behaves identically to the native protein with regard to enzyme activity. The clone that contains the full-length ACS cDNA showed higher enzyme activity (94%) compared to enzymatic activity of the wild type vector (Table 2). In addition, the purified ACS antibody was capable of removing the ACS activity of the recombinant ACS fusion protein and also from a heart mitochondrial extract.

Southern blot analysis and gene structure

ACS appears to be a single copy gene. A single hybridizing band was seen in the bovine EcoRI genomic digests which have been analyzed by southern blot analysis. This result and the fact that full-length ACS cDNA does not contain EcoRI sites rules out the possibility of more than one gene copy. Analysis of the ATC5 5' end, and sequence of the ACS genomic DNA will provide information necessary to determine the organization of ACS, and where introns are located.

Both the full-length ACS cDNA and the 228 bp fragment hybridized with the fungal ACS gene. This hybridization occurred under high stringency. This indicates high homology between the bovine and fungal ACS genes. Also, this result suggests that the ACS gene is a conserved gene. Hiroyuki, T., Protein Seq. Data Anal. 4:111–117 (1991) extracted a conservative sequence motif from the alignment of the firefly luciferase family. Acetyl-CoA synthetase derived from $N.$ $crassa$ and $A.$ $nidulans$ was identified as a member of the firefly luciferase family. The motif sequence shares several characteristics with the phosphoproteins and the nucleotide-binding proteins of the luciferase family.

Northern blot analysis of ACS mRNA

Another interesting, yet unexpected, result was the detection of multiple forms of ACS mRNA. This result suggests that this gene is differently controlled in different bovine tissue. The level of ACS mRNA is low relative to the level of ACS protein in the cell (0.001% of total mammary protein). This suggests that the ACS mRNA is efficiently translated. The existence, in ruminant tissue, of several forms of ACS mRNA does not necessarily mean that the enzyme coding sequence is different.

Acetyl-CoA synthetase mRNA is very low (FIGS. 19A and 19B). Therefore, for further study it may be necessary to amplify ACS mRNA using PCR and ACS specific probes.

Slot blot analysis

Milk production involves the coordinated regulation of many genes. Acetyl-CoA synthetase transcription was higher at 120 days postpartum than in 60, 180 or in the dry gland. ACS activity is marginal in a dry mammary gland, increases from parturition to peak milk production and then declines in activity as lactation advances (Marinez, D. S., et al., J. Agric. Food Chem. 24:927 (1976)) which agrees with the slot blot results (FIG. 25). These results suggest that the expression of this gene is very tightly controlled.

Changes in ACS mRNA level suggest that there is regulation at the transcription level. Therefore, the regulatory regions would be located up stream from the 5' end. The upstream regulatory regions (URE) are short sequences in the promoter that act as binding sites for proteins that can interact either directly or indirectly with transcription factors (TF) or other proteins in the transcription complex in order to facilitate complex formation and/or RNA polymerase II binding (Klein-Hitpass, L., et al., Cell 60:247–257 (1990)). URE can affect transcription even when they are positioned some distances from the transcription start site (Struhl, K. Cell. 49:295–297 (1987)). However, it has been found that when such sequences were placed at varying distances from the start site, full activity was only observed when the distance to the TATA box was altered in multiples of ten to eleven bases (Takahashi, K., et al., Nature 319:121–126 (1989)). This suggests that the URE binding proteins must be present in a specific orientation for enhanced RNA polymerase activity, and that this requirement may be fulfilled if there is sufficient distance between the URE and the site of complex formation.

More work can be done to be certain that the ACS gene is transcriptionally regulated. This could be done by screening a bovine genomic library with an oligo made from the 5' ATC5 cDNA nontranslated region. Isolated genomic fragments containing the regulatory regions would be able to express a reporter gene.

The northern blot was probed with β-actin to check for mRNA integrity and quantity (FIG. 18). However, it is recognized that β-actin is not a good indicator for mammary gland mRNA. Binding of β-actin to mRNA from mammary gland 180 days postpartum was quite low. This low binding might be due to the involution of mammary gland at late lactation.

Western blot analysis

To confirm that the rabbit anti-bovine acetyl-CoA synthetase binds to a biologically active ACS, and to demonstrate ACS tissue-specific expression, western blots were made of mitochondrial tissue extracts from heart, liver, mammary gland, kidney and spleen. Spleen mitochondrial extract was used in this experiment as a negative control. Spleen does not have ACS activity, however, it has a high level of acetyl-CoA hydrolase. Acetyl-CoA synthetase purified antibody bound to a single band in the tissues that express ACS (heart, kidney, and mammary gland). The band size was 65 kD. This molecular weight agrees with the known ACS molecular weight. These results, in addition to those of the enzyme assay show that rabbit anti-bovine ACS has a high affinity for ACS. In addition the purified antibody did not bind to protein from the liver mitochondrial extract. On the other hand the purified antibody did bind to a 78 kD band in the spleen mitochondrial extract. We do not have an explanation for the spleen band but we think it represents nonspecific binding.

Acetyl-CoA synthetase tissue specific-expression can be studied by finding and characterizing the regulatory regions and the proteins which bind them. Then, the factors which influence the presence, the activation, and the binding of these proteins to the regulatory regions could be determined. Such factors include the spatial and temporal regulation of the expression of the genes which encode these DNA binding proteins, and also the proteins involved in the phosphorylation or the post-transcriptional modifications of these protein factors which may alter there ability to bind to their specific sequences or alter their ability to interact appropriately with the RNA. For example, the chromatin structure in and around the promoter has been demonstrated to alter the binding pattern of the essential components of the mRNA transcription complex (Laybourn, J. and J. Kadonaga, Science. 254:238–244 (1991)). Finally, the spatial orientation and packing of the chromatin within the nucleus and the channels through it may even play a role by determining which mRNA is allowed to leave the nucleus and which are physically blocked by the proteins and DNA (Blobel, G., Gene gatting: A hypothesis. PNAS. 83:8527–8529 (1985); Chang, D. and P. Sharp, Science. 249:614–615 (1990)).

ATC5 Sequence

The ATC5 cDNA was subcloned into pUC19 at the EcoRI site, and the insertion was confirmed by EcoRI digestion of the recombinant pUC19-ATC5 DNA and analysis in agarose gel (FIG. 17). The corresponding double stranded pUC19-ATC5 DNA, as the template, was sequenced in one direction using the dideoxy chain termination method. The sequencing strategy is shown in FIG. 23.

ATC5 sequence is shown in FIGS. 26A-1 and 26A-2. Only 1130 bp were sequenced at the 5' end and 261 bp at the 3' end. The EcoRI recognition sequence, 5'-GAATTC-3', at the 5' and the 3' end was found. Also a potential poly adenylation site (ATAAA) is detected at the 3'end. The GC content of ATC5 is 58%. The cloned ACS cDNA is 4.2 kb. However the expected size of bovine ACS is about 2 kb. Many cDNA are much larger than the coding region. For example, the reported size of bovine retinal pigment epithelium cDNA is 3115 bp, with a coding region of 1549 bp (Hamel, C. P., et al., Molecular cloning and expression of RPE65, a novel retinal pigment epithelium-specific microsomal protein that is post-transcriptionally regulated in vitro. J. B. C. 268:15751–15757 (1993)). Out of the 1566 nontranslated bp, 1514 bases were located at the 3' end and 52 bases at the 5' end. Also, the mouse liver murine S-adenosyl methionine synthetase was cloned and sequenced (Shigeko, F. S., et al, Cloning and expression of murine S-Adenosylmethionine synthetase. J. B. C. 268:13978–13986 (1993)). The cDNA was 3232 bp with a coding region of 1188 bp. Out of the 2044 nontranslated bp 1820 bp were located at the 3' end and 224 bp were located at the 5' end. Therefore,it is not uncommon for a cDNA to be much larger than the coding region. Most of the untranslated region is at the 3' end.

A comparison of the ATC5 restriction map with the restriction maps of all the vectors (λgt11, pUC19, pGEM-3Z, and pEMBL8) and fungal DNA used in this project showed that ATC5 is not related to any of these.

ATC5 has 42% homology with the *N. crassa* ACS gene, and the amino acid homology was 9%. The 42% homology is significant; however the 9% homology is very low. Since ATC5 is sequenced in only one direction, a missing bp would not affect the nucleic acid homology, but would result in a major change in the predicted ACS amino acid sequence.

In vitro translation

Earlier studies of acetyl-CoA synthetase indicated that the protein is 63 kD. Therefore, a full length cDNA should encode a protein of 572 amino acids. The native ACS is N-glycosylated. However, the in vitro translation product is not. The lack of glycosylation in the in vitro transcription\translation system explains molecular weight difference between the native and the expressed ACS (about 10 kD).

The main objective of the in vitro translation experiment was to identify the ATC5 5' end. ATC5 was cloned into pGEM-3Z plasmid, and two reporter reactions were performed. The first reaction contained T7 RNA polymerase, and the other contained SP6 RNA polymerase. Activation of T7 promoter produced a protein; however, SP6 did not. These results suggest that the 5' end of ATC5 fragment is under the control of the T7 promoter. This conclusion was further supported by sequencing. To orient ATC5, pGEM-3Z-ATC5 was cut with ScaI and BamHI. Comparing the size of resulted fragments with ATC5 and pGEM-3Z restriction map indicated that the EcoRI-BamHI end is the 5' end of ATC5.

ACS fusion protein enzyme assay

*E.coli* infected with wild type λgt11 would produce β-galactosidase as a fusion protein. While, *E. coli* infected with λgt11-ATC5 would produce β-galactosidase-acetyl-CoA synthetase as a fusion protein. The expression vector λgt11 makes a temperature sensitive repressor (c1857) which is inactive at 42° C. and has an amber mutation (S100) which only lyses the hosts containing the amber suppressor supF. On the other hand, *E. coli* Y1089 has a lac repressor which inhibits LacZ gene expression until derepressed by IPTG, also it is deficient in protease which decreases the degradation of the recombinant fusion protein, and supF which suppresses the phage mutation (S100) (Young, R. A. and R. W. Davis, Science. 222:778 (1983)). Thus, λgt11 will not lyse Y1089 at 30° C. because of its C1857 mutation, and lacZ won't be expressed until the addition of IPTG. Taking advantage of these characteristics, we successfully induced the *E. coli* 1089 lysogen strains by infecting the cell with recombinant λgt11 and obtained sufficient acetyl-CoA synthetase-β-galactosidase fusion protein for enzyme assay.

The bovine ACS cDNA was expressed in *E. coli* to verify cloning and functional integrity of recombinant acetyl-CoA synthase. The ACS enzyme activity in infected *E. coli* was inhibited by rabbit anti-bovine ACS and β-galactosidase monoclonal antibody. In addition recombinant ACS enzyme activity was 2 fold greater than the wild type λgt11 protein. These results suggest that recombinant ACS is a functionable protein, and ATC5 is coded for the whole ACS gene. *E. coli* expressed a low but detectable level of ACS activity. The rabbit anti-bovine ACS was not capable of removing the bacterial ACS activity. This data shows that the rabbit anti-bovine ACS is highly specific to the bovine protein.

The fusion protein produced from *E. coli* infected with λgt11-ATC5 showed 94% increase in enzyme activity. Also, the fusion protein produced by the *E. coli* infected with λgt11-AR8 reacted with ACS and β-galactosidase antibody.

Summary

The results from this invention have advanced the field of ruminant metabolism. Also, they have provided the tools (namely the bovine ACS gene and the bovine mammary cDNA library) for future studies of how ruminant animals alter gene expression in response to lactation. The bovine ACS gene has been cloned and characterized. The ACS gene has a single copy per haploid chromosome. Acetyl-CoA synthetase enzyme assay results provide evidence that the recombinant ACS is biologically active like the native protein. In addition, the ACS purified antibody is highly specific to ACS. It is believed that this is the first report of recombinant mammalian ACS.

The fact that lactation can have an effect on ACS gene expression has been directly demonstrated by the slot blot study. Further, data have been presented which provides strong evidence of alternative promoters and\or alternative splicing involved in ACS gene regulation. Finally, the data suggests that ACS is controlled at both the transcriptional and post transcriptional level.

From a biological aspect, the cloning of the bovine ACS makes it possible to study the biochemical events that occur in order to bring about altered gene expression in response to Lactation, hormones and different metabolic conditions. From a more physiological aspect, the cloning of bovine ACS makes it possible to test the role of the ACS gene in milk production by utilizing antisense technology to reduce the function of ACS in lactating animal at peak lactation. These studies of the ACS gene can shed light on the biological control of other acyl-CoA synthetases (e.g. propionyl-CoA synthetase).

In addition, the isolation of the bovine ACS promoter(s) is now possible and this may well prove quite valuable in the field of transgenics. The fact that there is tissue specific expression of ACS makes its promoter a good candidate for gene regulation studies.

Finally, there is recent evidence for cross-talk between separate signal transduction pathways (Nishizuka, Y., Signal transduction:Crosstalk. TIBS. 17:367–376 (1992)). Also, there may be several signal transduction pathways that play a role in the regulation of the genes involved in milk production. Thus, these initial studies of the molecular biology of lactation-regulated genes, may provide a starting point for studies of the interaction and the communication between the various signal transduction pathways involved in milk production. The experiments and fields of study discussed in this invention will add greatly to understanding of ruminant gene regulation, biochemistry, and physiology. Further, the invention can be used to select for animals which have low levels of ACS expression, particularly in populations of animals.

The foregoing description is only illustrative of the present invention and the present invention is limited only by the hereinafter appended claims.

We claim:

1. A method for determining potential for milk production of a bovine as a calf before milk production and breeding which comprises:
    (a) determining a level of acetyl coenzyme A synthetase (ACS) or mRNA from mammary tissue of the calf and
    (b) estimating the milk production potential of the calf based upon the ACS.

2. A method for determining potential for milk production in a population of bovines as calves before milk production for subsequent breeding purposes which comprises:
    (a) determining a level of acetyl coenzyme A synthetase (ACS) or mRNA from mammary tissue in the calves before milk production and breeding;
    (b) estimating the milk production potential of the calves in the population based upon the ACS;
    (c) selecting the calves from the population from breeding for milk production; and
    (d) breeding the selected calves as adults.

3. The method of claim 2 wherein the mRNA is determined using a DNA probe for the mRNA encoding the ACS.

4. The method of claim 2 wherein the ACS is determined using an antibody to the ACS.

5. The method of claim 2 wherein the calves are from a milk producing breeding line.

6. The method of claim 2 wherein the mRNA is determined using a DNA probe encoding the ACS and wherein the DNA is contained in pUC19-AR8 deposited as ATCC 29191.

7. The method of claim 3 wherein the DNA is selected from the group consisting of SEQ ID NO:3 and SEQ ID NO:4.

* * * * *

UNITED STATES PATENT AND TRADEMARK OFFICE
CERTIFICATE OF CORRECTION

Page 1 of 3

PATENT NO. : 5,981,187
DATED : November 9, 1999
INVENTOR(S) : Robert M. Cook, et. al.

It is certified that error appears in the above-identified patent and that said Letters Patent is hereby corrected as shown below:

Title page, in the Abstract, line 1, "deterining" should be --determining--.

Column 1, lines 8 to 20 should be deleted and the original paragraph inserted as follows: -- The present invention relates to a method for the determination of milk production potential in bovines. In particular the present invention relates to a method wherein a level of acetyl coenzyme A synthetase (ACS) in mammary tissue is determined to provide the estimate and wherein the bovine is selected for milk production based upon the ACS level. The method is particularly valuable for estimating potential for milk production in calves at an early date. The method is also particularly useful in breeding selection where the maternal parents exhibit high ACS activity.--

Column 4, line 27, "a" after "are" and before "photographs" should be deleted.

Column 4, line 60, "acid" after "nucleotide" and before "sequences" should be deleted.

Column 5, line 29, "α32P ATC5" should be --$\alpha^{32}$P ATC5--.

Column 5, line 34, "a" after "are" and before "photographs" should be deleted.

UNITED STATES PATENT AND TRADEMARK OFFICE
CERTIFICATE OF CORRECTION

PATENT NO. : 5,981,187
DATED : November 9, 1999
INVENTOR(S) : Robert M. Cook, et. al.

It is certified that error appears in the above-identified patent and that said Letters Patent is hereby corrected as shown below:

Column 6, line 27, "is of nucleotide 215 (M)" should be --is at nucleotide 897(N)--.

Column 8, line 58, after "that" and before "was" insert --there--.

Column 16, line 23, "minutes at 40°C" should be --minutes at 4°C--.

Column 18, line 20, "2XSCC" should be --2XSSC--.

Column 18, line 36, "20XSCC" should be --20XSSC--.

Column 19, line 42, "ATCS)." should be --ATC5).--.

Column 24, line 6, "lysogenies" should be --lysogenes--.

Column 24, line 9, "tittered" should be --titered--.

Column 25, line 60, "EcorI site" should be --EcoRI site--.

Column 29, line 46, "N-linked suger" should be --N-linked sugar--.

Column 31, line 34, "there ability" should be --their ability--.

Column 33, line 3, "synthase." should be --synthetase.--.

UNITED STATES PATENT AND TRADEMARK OFFICE
CERTIFICATE OF CORRECTION

PATENT NO. : 5,981,187
DATED : November 9, 1999
INVENTOR(S) : Robert M. Cook, et. al.

It is certified that error appears in the above-identified patent and that said Letters Patent is hereby corrected as shown below:

Column 34, line 10, "acyl-CoA" should be --acetyl-CoA--.

Signed and Sealed this

Fourteenth Day of November, 2000

*Attest:*

Q. TODD DICKINSON

*Attesting Officer*     *Director of Patents and Trademarks*

UNITED STATES PATENT AND TRADEMARK OFFICE
CERTIFICATE OF CORRECTION

PATENT NO. : 5,981,187
DATED : November 9, 1999
INVENTOR(S) : T. Sakata et al.

It is certified that error appears in the above-indentified patent and that said Letters Patent is hereby corrected as shown below:

At column 9, line 3 (claim 10, line 3) after "grommet" delete " , ".

Signed and Sealed this

Twentieth Day of March, 2001

Attest:

NICHOLAS P. GODICI

*Attesting Officer*  *Acting Director of the United States Patent and Trademark Office*

UNITED STATES PATENT AND TRADEMARK OFFICE
CERTIFICATE OF CORRECTION

PATENT NO. : 5,981,187
DATED : November 9, 1999
INVENTOR(S) : Robert M. Cook, et al.

It is certified that error appears in the above-identified patent and that said Letters Patent is hereby corrected as shown below:

This certificate supercedes Certificate of Correction issued March 20, 2001, the number was erroneously mentioned and should be deleted since no Certificate of Correction was granted.

Signed and Sealed this

Eleventh Day of September, 2001

*Attest:*

*Attesting Officer*

NICHOLAS P. GODICI
*Acting Director of the United States Patent and Trademark Office*